(12) United States Patent
Hodges et al.

(10) Patent No.: US 8,895,624 B2
(45) Date of Patent: Nov. 25, 2014

(54) TREATMENT OF OSTEOPOROSIS

(75) Inventors: Stephen Hodges, Essex (GB); Robin Soper, Essex (GB)

(73) Assignee: Haoma Medica Ltd., Essex (GB)

( * ) Notice: Subject to any disclaimer, the term of this patent is extended or adjusted under 35 U.S.C. 154(b) by 0 days.

(21) Appl. No.: 13/518,621

(22) PCT Filed: Dec. 22, 2010

(86) PCT No.: PCT/GB2010/052195
§ 371 (c)(1),
(2), (4) Date: Jun. 22, 2012

(87) PCT Pub. No.: WO2011/077159
PCT Pub. Date: Jun. 30, 2011

(65) Prior Publication Data
US 2013/0030050 A1 Jan. 31, 2013

(30) Foreign Application Priority Data
Dec. 23, 2009 (GB) .................................. 0922513.7

(51) Int. Cl.
*A61K 31/12* (2006.01)
*C07C 49/105* (2006.01)
*A61K 31/122* (2006.01)
*A61K 31/00* (2006.01)

(52) U.S. Cl.
CPC ............... *A61K 31/122* (2013.01); *A61K 31/00* (2013.01)
USPC ........... 514/682; 514/675; 514/678; 568/328; 560/51; 560/53

(58) Field of Classification Search
CPC .................................................... A61K 31/122
USPC .......................................... 514/675, 678, 682
See application file for complete search history.

(56) References Cited

U.S. PATENT DOCUMENTS

2005/0222258 A1   10/2005   Wang

FOREIGN PATENT DOCUMENTS

| EP | 0123238 A2 | 10/1984 |
|----|------------|---------|
| EP | 0123238 B1 | 6/1987 |
| EP | 1889613 A | 2/2008 |
| GB | 2314773 | 1/1998 |
| WO | WO03/013420 | 2/2003 |

OTHER PUBLICATIONS

Sano et al., "Metabolic fate of menaquinone-4 in dogs. (I). Absorption, distribution, metabolism and excretion after a single oral administration", 1997, Yakubutsu Dotai, 12(1), pp. 48-57.*

Fleming et al., "Bone structure and strength at different ages in laying hens and effects of dietary particulate limestone, vitamin K and ascorbic acid", 1998, British Poultry Science, vol. 39, pp. 434-440.*

Yamaguchi et al., "Stimulatory effect of menaquinone-7 on bone formation in elderly female rat femoral tissues in vitro: Prevention of bone deterioration with aging", 2002, Internationaljournal of Molecular Medicine, vol. 10, pp. 729-733.*

* cited by examiner

*Primary Examiner* — My-Chau T Tran
(74) *Attorney, Agent, or Firm* — Cooley LLP

(57) ABSTRACT

According to the invention there is provided a compound of formula (I): wherein $R^1$, $R^2$, $R^3$ and n have meanings given in the description, or a pharmaceutically acceptable solvate, salt or prodrug thereof for use in the treatment of osteoporosis and/or osteopenia.

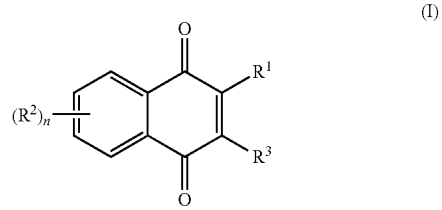

(I)

27 Claims, 20 Drawing Sheets

Inhibition of γ-carboxylase by KCAT-5C (XIV) in the presence of 220μM vitamin $K_1$ hydroquinone (n=1)

Inhibition of γ-carboxylase by KCAT-5C-Me (XIX) in the presence of 220μM vitamin $K_1$ hydroquinone (n=1)

Inhibition of γ-carboxylase by NaQuinate (VIII) in the presence of 220μM vitamin $K_1$ hydroquinone (n=1)

Inhibition of γ-carboxylase by NaQuinate-Me (VII) in the presence of 220μM vitamin $K_1$ hydroquinone (n=1)

Inhibition of γ-carboxylase by QCAT-Me (XVIII) in the presence of 220μM vitamin $K_1$ hydroquinone (n=1)

Inhibition of γ-carboxylase by DMK (XVI) in the presence of 220μM vitamin $K_1$ hydroquinone (n=1)

Inhibition of γ-carboxylase by Vitamin $K_3$ (III) in the presence of 220μM vitamin $K_1$ hydroquinone (n=1)

NaQuinate does not alter normal bone trabecular number
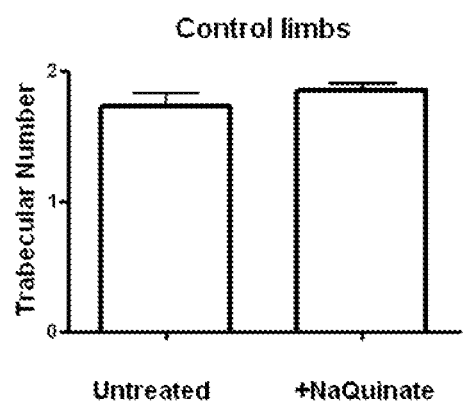
Fig 17    The trabecular number from unoperated (control) mice tibia.

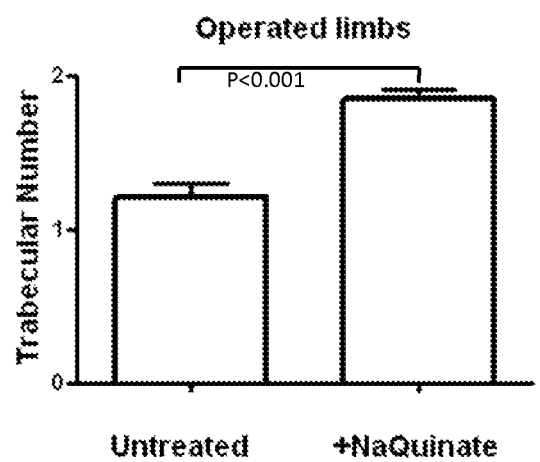
Fig 18    The trabecular number from neurectomized mice tibia.

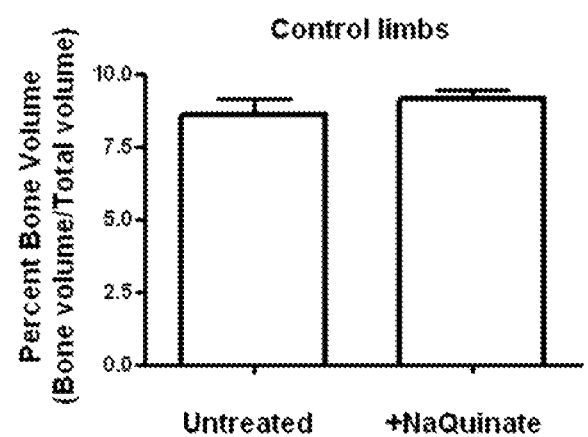
Fig 19. Percent bone volume from unoperated (control) mice tibia.

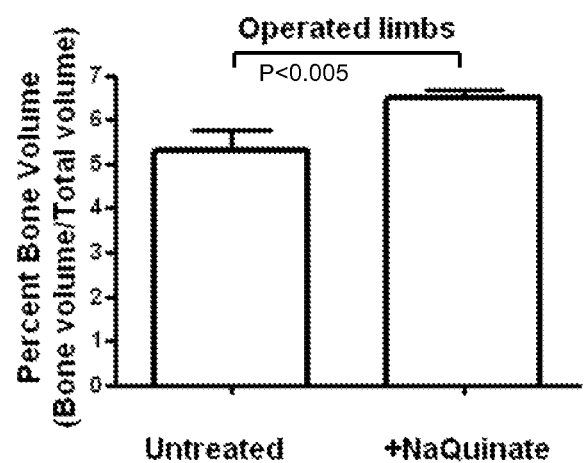
Fig 20. Percent bone volume from neurectomized mice tibia.

TREATMENT OF OSTEOPOROSIS

CROSS REFERENCE TO RELATED APPLICATIONS

This application is the national phase entry under 35 U.S.C. §371 of PCT/GB2010/052195, filed Dec. 22, 2010, which claims priority under 35 U.S.C. §119(b) from GB Application No. 0922513.7, filed Dec. 23, 2009, which are both incorporated herein by reference in their entireties.

FIELD OF INVENTION

The present invention relates to compounds for use in the treatment of osteoporosis and osteopenia, and combinations comprising said compounds.

Osteoporosis is a disease of bone that leads to an increased risk of fracture. In osteoporosis the bone mineral density (BMD) is reduced, bone microarchitecture is disrupted, and the amount and variety of non-collagenous proteins in bone is altered. The World Health Organization define osteoporosis (in women) as a bone mineral density 2.5 standard deviations below peak bone mass (30-year-old healthy female average). Osteoporosis is most common in women after menopause, when it is called postmenopausal osteoporosis, but may also develop in men, and may occur in anyone in the presence of particular hormonal disorders and other chronic diseases or as a result of medications, specifically glucocorticoids, when the disease is called steroid- or glucocorticoid-induced osteoporosis and as a result of nutritional deficiency states or other metabolic disorders, including, but not limited to, hyponatremia or as a secondary consequence of cancer. Given its influence on the risk of fragility fracture, osteoporosis may significantly affect life expectancy and quality of life.

Osteopenia is a condition where bone mineral density is lower than normal. It is considered by many doctors to be a precursor to osteoporosis. More specifically, osteopenia is defined as a bone mineral density T score between −1.0 and −2.5. Furthermore, osteopenia can be induced under specific conditions such as long-term bed rest or spending extended time in a microgravity environment, such as near-Earth orbit or space flight.

The underlying mechanism in all cases of osteoporosis is an imbalance between bone resorption and bone formation. In normal bone, there is constant matrix remodelling of bone; up to 10% of all bone mass may be undergoing remodelling at any point in time. Bone is resorbed by osteoclast cells (which are derived from bone marrow precursor cells). In the remodelling process new bone is deposited by osteoblast cells.

The three main mechanisms by which osteoporosis develops are: an inadequate peak bone mass (the skeleton develops insufficient mass and strength during growth), excessive bone resorption and inadequate formation of new bone during remodelling. Interplay of these three mechanisms underlies the development of fragile bone tissue. Hormonal factors strongly determine the rate of bone resorption; lack of oestrogen (e.g. as a result of menopause) increases bone resorption as well as decreasing the deposition of new bone that normally takes place in weight-bearing bones. The α-form of the oestrogen receptor appears to be the most important in regulating bone turnover. In addition to oestrogen, calcium metabolism plays a significant role in bone turnover, and deficiency of calcium and vitamin D leads to impaired bone deposition; in addition, the parathyroid glands react to low calcium levels by secreting parathyroid hormone, which increases bone resorption to ensure sufficient calcium in the blood.

Osteoporosis can be limited in extent of development by lifestyle changes and medication; in people with osteoporosis, treatment may involve both. Lifestyle change includes adequate balanced nutrition, preventing falls and exercise. Existing medication includes calcium, vitamin D, vitamin K, bisphosphonates, Calcitonin, Teriparatide, Strontium ranelate, hormone replacement and selective oestrogen receptor modulators.

In confirmed osteoporosis, bisphosphonate drugs are often the first-line treatment. The most often prescribed bisphosphonates are presently sodium alendronate (Fosamax™) orally, risedronate (Actonel™) orally or etidronate (Didronel™) orally, or ibandronate (Boniva™) orally daily or once a month or zolendronate (Zometa™) monthly or yearly intravenously or Pamidronate (Aredia™) monthly or 3-6 monthly intravenously. Oral bisphosphonates are relatively poorly absorbed, and must therefore be taken on an empty stomach, at least 30 minutes prior to a meal/drink. They are also associated with oesophagitis and are therefore poorly tolerated; weekly or monthly administration decreases likelihood of oesophagitis. However intermittent dosing with intravenous formulations such as zolendronate are implicated in a rare but unpleasant mouth disease called osteonecrosis of the jaw.

Teriparatide has a limited time course for use in osteoporosis treatment efficacy but in many countries is only licensed for treatment if bisphosphonates have failed or are contraindicated; and young patients or those with previous radiation therapy, or Paget's disease should avoid this medication.

Oral strontium ranelate is an alternative oral treatment, suggested to stimulate the proliferation of osteoblasts, as well as inhibiting the proliferation of osteoclasts. However it increases the risk of venous thromboembolism so is less suitable in patients at risk for thrombosis for different reasons. Also Strontium must not be taken with food or calcium-containing preparations as calcium competes with strontium during uptake. However, it is essential that calcium, magnesium, and vitamin D in therapeutic amounts must be taken daily, but not at the same time as strontium.

Oestrogen replacement therapy remains a good treatment for prevention of osteoporosis but, at this time, is not universally recommended unless there are other indications for its use as well. There is uncertainty and controversy about whether oestrogen should be recommended in women in the first decade after the menopause.

There is therefore a need for a new treatment for the osteoporosis and osteopenia that overcomes shortcomings in the treatments previously available.

It has now surprisingly been found that certain naphthoquinone compounds are able to inhibit bone loss and may provide a beneficial treatment for osteoporosis and/or osteopenia.

The present invention relates to compounds of formula (I)

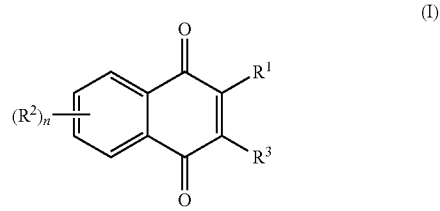

wherein:

$R^1$ represents hydrogen, halogen, cyano, trifluoromethyl, nitro, —$OR^a$, $SR^a$, $SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$, —$CONR^aR^b$, or a hydrocarbon group comprising a straight chain, branched or cyclic group each containing up to 18 carbon atoms, or a heterocyclic group containing up to 18 carbon atoms and at least one heteroatom;

$R^2$ represents, independently at each occurrence, hydrogen or, more particularly, halogen, cyano, trifluoromethyl, nitro, —$OR^a$, $SR^a$, $SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$, —$CONR^aR^b$, or a hydrocarbon group comprising a straight chain, branched or cyclic group each containing up to 18 carbon atoms, or a heterocyclic group containing up to 18 carbon atoms and at least one heteroatom (e.g. $R^1$ or $R^2$ represents hydrogen, halogen, cyano, trifluoromethyl, nitro, —$OR^a$, $SR^a$, $SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$, —$CONR^aR^b$, or a hydrocarbon group comprising a straight chain, branched or cyclic group each containing up to 18 carbon atoms, or a heterocyclic group containing up to 18 carbon atoms and at least one heteroatom);

$R^3$ represents a hydrocarbon group comprising a straight chained, branched or cyclic group each containing up to 18 carbon atoms, and being substituted by at least one moiety including a —$CO_2R^a$ substituent;

wherein $R^a$ and $R^b$ independently represent, at each occurrence, hydrogen, or a hydrocarbon group comprising a straight chained, branched or cyclic group each containing up to 18 carbon atoms, or a heterocyclic group containing up to 18 carbon atoms and at least one heteroatom (e.g. wherein $R^a$ and $R^b$ independently represent hydrogen, or a hydrocarbon group comprising a straight chained, branched or cyclic group each containing up to 18 carbon atoms, or a heterocyclic group containing up to 18 carbon atoms and at least one heteroatom);

n is 0 or, more particularly, 1, 2, 3 or 4;

or a pharmaceutically acceptable salt or prodrug thereof;

for use in the manufacture of a medicament for the treatment of osteoporosis, or for use in the treatment of osteoporosis and/or osteopenia.

Reference to use in osteoporosis herein is taken to include reference to osteopenia, unless otherwise specified or apparent.

Another aspect of the present invention provides pharmaceutical compositions comprising a compound of formula (I) with a pharmaceutically acceptable carrier. In a further aspect of the present invention, there is provided a pharmaceutical composition comprising a compound of formula (I) and a pharmaceutically acceptable carrier, diluent or excipient therefor, for the treatment of osteoporosis and/or osteopenia, and for use in combinations as described herein.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula (I), additional active ingredient(s), and pharmaceutically acceptable excipients.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients. Suitable pharmaceutical compositions may be found in, for example, Remington *The Science and Practice of Pharmacy*, 19th ed., Mack Printing Company, Easton, Pa. (1995). For parenteral administration, a parenterally acceptable aqueous solution may be employed, which is pyrogen free and has requisite pH, isotonicity, and stability. Suitable solutions will be well known to the skilled person, with numerous methods being described in the literature. A brief review of methods of drug delivery may also be found in e.g. Langer, *Science* (1990) 249, 1527.

Reference to the compound of formula (I) herein is taken to include reference to all pharmaceutically acceptable salts, prodrugs or tautomers, unless otherwise apparent from the context. Accordingly in its broadest aspect the present invention relates to compounds of formula (I) or a pharmaceutically acceptable salt, prodrug or tautomer thereof, for use in the treatment of, and the manufacture of medicaments for the treatment of, osteoporosis and/or osteopenia.

The term "pharmaceutically acceptable salts" refers to salts prepared from pharmaceutically acceptable non-toxic bases including inorganic bases and organic bases (for example, given the presence of substituent —$CO_2R^a$ present in $R^3$), or salts prepared from pharmaceutically acceptable non-toxic acids including inorganic acids and organic acids (for example, in the case where a basic substituent is present in any of $R^1$ or $R^2$).

Salts derived from inorganic bases include aluminum, ammonium, calcium, copper, ferric, ferrous, lithium, magnesium, potassium, sodium, zinc, and the like. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, morpholine, piperazine, piperidine, polyamine resins, procaine, purines, theobromine, triethylamine, trimethylamine, tripropylamine, and the like.

Salts derived from acids include acetic, benzenesulfonic, benzoic, camphorsulfonic, citric, ethanesulfonic, fumaric, glutamic, hydrobromic, hydrochloric, isethionic, lactic, maleic, mandelic, methanesulfonic, nitric, pamoic, pantothenic, phosphoric, succinic, sulfuric, tartaric, p-toluenesulfonic acid, and the like.

As mentioned above, also encompassed by formula I are any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulphoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates. Particularly preferred solvates are hydrates, and examples of hydrates include hemihydrates, monohydrates and dihydrates.

For a more detailed discussion of solvates and the methods used to make and characterise them, see Bryn et al., *Solid-State Chemistry of Drugs*, Second Edition, published by SSCI, Inc of West Lafayette, Ind., USA, 1999, ISBN 0-967-06710-3.

The present invention also includes within its scope the use of prodrugs of the compounds of formula (I). In general, such prodrugs are functional derivatives of the compounds of formula (I) which are readily convertible in vivo into the required compound. Conventional procedures for the selection and preparation of suitable prodrug derivatives are well known in the art. The term "prodrug" of a relevant compound of formula I includes any compound that, following administration (e.g. oral or parenteral administration), is metabolised in vivo to form that compound in an experimentally-detectable amount, and within a predetermined time (e.g. within a dosing interval of between 6 and 24 hours (i.e. once to four times daily)).

Prodrugs of compounds of formula I may be prepared by modifying functional groups present on the compound in such a way that the modifications are cleaved, in vivo when such prodrug is administered to a mammalian subject. The modifications typically are achieved by synthesizing the parent compound with a prodrug substituent. Prodrugs include compounds of formula I wherein a hydroxyl, amino, sulfhydryl, carboxyl or carbonyl group in a compound of formula I is bonded to any group that may be cleaved in vivo to regenerate the free hydroxyl, amino, sulfhydryl, carboxyl or carbonyl group, respectively.

Examples of prodrugs include, but are not limited to, esters and carbamates of hydroxyl functional groups, esters groups of carboxyl functional groups, N-acyl derivatives and N-Mannich bases. General information on prodrugs may be found e.g. in Bundegaard, H. "Design of Prodrugs" p. 1-92, Elsevier, New York-Oxford (1985).

In one aspect the prodrug is not vitamin K. Unless otherwise stated, the term "vitamin K" as used herein relates to vitamin $K_1$ and vitamin $K_2$ collectively and not to man-made analogues of vitamin K.

Compounds of formula I may contain double bonds and may thus exist as E (entgegen) and Z (zusammen) geometric isomers about each individual double bond. All such isomers and mixtures thereof are included within the scope of the invention.

Compounds of formula I may exist as regioisomers and may also exhibit tautomerism. All tautomeric forms and mixtures thereof are included within the scope of the invention.

Compounds of formula I may contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person. All stereoisomers and mixtures thereof are included within the scope of the invention.

The compound of formula (I), or pharmaceutical compositions comprising the compound of formula (I), for use mentioned in the above-mentioned aspects of the invention may be utilised in a method of medical treatment. Thus, according to further aspects of the invention, there is provided a method of treatment or prevention of osteoporosis and/or osteopenia, which method comprises the administration of an effective amount of a compound of formula (I), or a pharmaceutical composition comprising the compound of formula (I), to a patient in need of such treatment.

Treatment of osteoporosis/osteopenia as disclosed herein includes prevention of bone loss, or attenuation of bone loss, or stimulation of bone growth, or an increase in bone density and also includes disuse osteoporosis, for example patients undergoing long term bed rest, those in low gravity conditions and paraplegics (e.g. Treatment of osteoporosis/osteopenia as disclosed herein includes prevention of bone loss, or attenuation of bone loss, or stimulation of bone growth, or an increase in bone density. It includes disuse osteoporosis, for example patients undergoing long term bed rest, those in low gravity conditions and paraplegics.)

Thus, in another aspect of the invention relates to the following.

(a) A compound of formula (I), or a pharmaceutical composition comprising a compound of formula (I), as herein before defined, for use in the prevention of bone loss, the attenuation of bone loss, the stimulation of bone growth, to produce an increase in bone density and to treat or prevent disuse osteoporosis (e.g. for example patients undergoing long term bed rest, those in low gravity conditions and paraplegics).

(b) Use of a compound of formula (I), or a pharmaceutical composition comprising a compound of formula (I), as hereinbefore defined, for the preparation of a medicament for the prevention of bone loss, the attenuation of bone loss, the stimulation of bone growth, to produce an increase in bone density and to treat or prevent disuse osteoporosis (e.g. for example patients undergoing long term bed rest, those in low gravity conditions and paraplegics).

(c) A method for the prevention of bone loss, the attenuation of bone loss, the stimulation of bone growth, to produce an increase in bone density and to treat or prevent disuse osteoporosis (e.g. for example patients undergoing long term bed rest, those in low gravity conditions and paraplegics), which method comprises the administration of an effective amount of a compound of formula (I), or a pharmaceutical composition comprising the compound of formula (I), to a patient in need of such treatment.

The invention relates to use of the compound of formula (I), or a pharmaceutical composition comprising a compound of formula (I), in the treatment of osteoporosis, including use in prevention of loss of bone density, use in the preparation of medicaments for such treatments and medical treatments in which the compound of the invention is administered to an individual in need of such treatment.

In one aspect the compound of formula (I), or a pharmaceutical composition comprising a compound of formula (I), is used in prevention of osteoporosis by prevention of the reduction of bone density, and is used in a prophylactic setting. Treatment may also be carried out in patients already suffering from osteoporosis, to prevent or reduce any decline in bone density.

Thus, a further aspect of the invention relate to the following.

(A) A compound of formula (I), or a pharmaceutical composition comprising a compound of formula (I), as hereinbefore defined, for use in the prevention or treatment of osteoporosis and/or osteopenia in a patient by:
  (a) preventing the reduction of bone density in a patient susceptible to osteoporosis and/or osteopenia; or
  (b) preventing or reducing any decline in bone density in a patient suffering from osteoporosis and/or osteopenia.

(B) Use of a compound of formula (I), or a pharmaceutical composition comprising a compound of formula (I), as hereinbefore defined, for the preparation of a medicament for the prevention or treatment of osteoporosis and/or osteopenia in a patient by:
  (a) preventing the reduction of bone density in a patient susceptible to osteoporosis and/or osteopenia; or
  (b) preventing or reducing any decline in bone density in a patient suffering from osteoporosis and/or osteopenia.

(C) A method for the prevention or treatment of osteoporosis and/or osteopenia in a patient by:
  (a) preventing the reduction of bone density in a patient susceptible to osteoporosis and/or osteopenia; or
  (b) preventing or reducing any decline in bone density in a patient suffering from osteoporosis and/or osteopenia,
which method comprises the administration of an effective amount of a compound of formula (I), or a pharmaceutical composition comprising the compound of formula (I), to a patient in need of such treatment.

In one aspect the use of the compound of the invention is for individuals who have reduced steroid hormones levels, for example reduced oestrogen levels in women, or reduced testosterone levels in men, or reduced dehydroepiandrosterone [DHEA] levels, compared to that at which normal bone density is maintained. In one aspect this is post menopausal women. In one aspect this is adults of greater than 50, 55, 60, 65 or greater than 70 years of age.

Thus the term, "patient susceptible to osteoporosis and/or osteopenia" as used herein may refer to:
  (i) patients who have reduced steroid hormones levels, for example reduced oestrogen levels in female subjects, or reduced testosterone levels in male subjects, or reduced dehydroepiandrosterone [DHEA] levels, compared to that at which normal bone density is maintained;
  (ii) post menopausal female patients;
  (iii) adult patients of greater than 50, 55, 60, 65 or greater than 70 years of age; and/or
  (iv) patients undergoing long term bed rest, those in low gravity conditions and/or paraplegic patients.

For the avoidance of doubt, in the context of the present invention, the term "treatment" includes references to therapeutic or palliative treatment of patients in need of such treatment, as well as to the prophylactic treatment and/or diagnosis of patients which are susceptible to the relevant disease states.

The terms "patient" and "patients" include references to mammalian (e.g. human) patients.

The term "effective amount" refers to an amount of a compound, which confers a therapeutic effect on the treated patient (e.g. sufficient to treat or prevent the disease). The effect may be objective (i.e. measurable by some test or marker) or subjective (i.e. the subject gives an indication of or feels an effect).

The term "halogen" as used herein includes fluorine, chlorine, bromine and iodine (e.g. bromine or, more particularly, chlorine of fluorine).

The term "hydrocarbon" as used herein with reference to any of $R^1$, $R^2$, $R^3$, $R^a$ and $R^b$ includes alkyl, alkenyl, alkynyl, cycloalkyl, alkyl, aryl, aryl-alkyl, aryl-alkenyl and aryl-alkynyl.

Suitable alkyl groups include straight chained or branched alkyl groups containing from 1 to 18 carbon atoms, or more preferably 1 to 9 carbon atoms. For example, typical examples can include methyl or ethyl, or straight chained or branched propyl, butyl, pentyl, hexyl, heptyl, octyl, nonyl or the like.

Suitable alkenyl groups include straight chained and branched alkenyl groups containing from 2 to 18 carbon atoms, and may include vinyl, allyl or isoprene moieties, 2-, 3- or 4-pentenyl, or 2-, 3-, or 4-hexenyl or the like, and isomeric forms thereof. Alkenyl groups as present in the compounds of the invention may include one or more degrees of unsaturation.

Suitable alkynyl groups include straight chained and branched alkynyl groups containing from 2 to 18 carbon atoms. For example, typical examples can include ethynyl and propynyl groups.

Suitable cycloalkyl groups include groups containing from 3 to 7 carbon atoms, for example cyclopropyl or cyclohexyl.

Suitable aryl groups can include aromatic hydrocarbon systems having one ring or two or three fused rings, such as phenyl or naphthyl. A particularly suitable aryl group can be phenyl.

Suitable heterocyclic groups can include ring systems having 5 or 6 ring atoms of which at least one ring atom is oxygen, sulphur or nitrogen. The ring systems can be aromatic or non-aromatic. Examples can include piperazinyl, morpholinyl, pyrrolyl, imidazolyl, thienyl, furanyl or other known heterocyclic ring systems.

According to a preferred embodiment of the present invention, $R^1$ represents a hydrocarbon group comprising a straight chain, branched or cyclic group each containing up to 18 carbon atoms. More preferably $R^1$ represents an alkyl group including straight chained or branched alkyl groups containing from 1 to 18 carbon atoms, or more preferably 1 to 9 carbon atoms (e.g. 1 to 6 carbon atoms, such as 1 to 5 carbon atoms). It is particularly preferred that $R^1$ represents methyl.

According to a further preferred embodiment of the present invention, n represents 0 or, alternatively, n is 4 and $R^2$, at each occurrence, is hydrogen (e.g. $R^2$ represents hydrogen and n is 4).

According to a still further preferred embodiment of the present invention, $R^3$ represents a hydrocarbon group comprising a straight chained or branched hydrocarbon group containing up to 18 carbon atoms, preferably an appropriate alkyl or alkenyl group, substituted by at least one moiety including a —$CO_2R^a$ substituent. More preferably, $R^3$ represents $C_{1-9}$ alkyl or $C_{2-9}$ alkenyl, which can be straight chained or branched, substituted by at least one moiety including a —$CO_2R^a$ substituent, wherein $R^a$ is substantially as hereinbefore defined. Preferably in the context of $R^3$, $R^a$ represents hydrogen, or a hydrocarbon group comprising a straight chained or branched hydrocarbon group containing up to 18 carbon atoms, preferably up to 9 carbon atoms, and even more preferably up to 6 carbon atoms. Preferably $R^a$ represents hydrogen or $C_{1-6}$ straight chained or branched alkyl, in particular methyl.

Preferably $R^3$ can be represented by the following formula (II)

where the unattached bond represents the point of attachment of the structural fragment of formula (II) to the rest of the compound of Formula (I);
$R^a$ is as hereinbefore defined;
where $R^c$, $R^d$ and $R^e$ are independently selected from hydrogen or $C_{1-6}$ alkyl (which can be straight chained or branched);
q is 1, 2, 3 or 4;
r and s are independently selected from 0, 1, 2, 3 or 4;
----- represents a single or double bond, and when this is a double bond $R^e$ is not present in above formula (II).

Preferably formula (II) represents a $C_{4-8}$ straight chained or branched alkyl group, or a $C_{4-8}$ straight chained or branched alkenyl group, substituted by —$CO_2R^a$, wherein preferably $R^a$ represents hydrogen or $C_{1-6}$ straight chained or branched alkyl, in particular methyl (e.g. $R^a$ when attached to $R^3$ represents H or $CH_3$).

Especially preferred groups represent by formula (II) include:

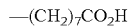

—$CH_2CH$=$C(CH_3)(CH_2)_2CO_2H$; and

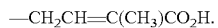

Specifically, the present invention provides one of more of the following compounds:
(i) 2,3-dimethoxy-1,4-naphthoquinone (XVI);
(ii) menadione (III);
(iii) KCAT-5C-Me (XIX);
(iv) NaQuinate-Me (VII);
(v) (4E)-6-(1,4-dihydro-2-methyl-1,4-dioxonaphthalen-3-yl)-4-methylhex-4-enoic acid (VIII);
(vi) (2E)-4-(1,4-dihydro-2-methyl-1,4-dioxonaphthalen-3-yl)-2-methylbut-2-enoic acid (XIV); and
(vii) 8-(1,4-dihydro-2-methyl-1,4-dioxonaphthalen-3-yl)octanoic acid (XV),
for use in the manufacture of a medicament for the treatment of osteoporosis and/or ostopenia, or for use in the treatment of osteoporosis and/or ostopenia.

For the avoidance of doubt, if there is a conflict between the given chemical name and the chemical structure, the chemical structure predominates.

Especially preferred is (4E)-6-(1,4-dihydro-2-methyl-1,4-dioxonaphthalen-3-yl)-4-methyl hex-4-enoic acid (VIII) for use in therapy according to the present invention substantially as hereinbefore described.

The present invention also provides novel compounds for use in therapy according to the present invention substantially as hereinbefore described. Specifically, these novel compounds are (2E)-4-(1,4-dihydro-2-methyl-1,4-dioxonaphthalen-3-yl)-2-methylbut-2-enoic acid (XIV) and 8-(1,4-dihydro-2-methyl-1,4-dioxonaphthalen-3-yl)octanoic acid (XV).

In one aspect the use of the compound of the invention may be as part of a combined therapy along with another therapeutic agent. In a further aspect the use of the compound of the invention in treatment of osteoporosis and/or osteopenia may be as part of a combined therapy along with another therapeutic agent.

Compounds of the invention may be used in combination with a bisphosphonate drug, teriparatide, strontium ranelate or oestrogen replacement therapy, vitamins, minerals or coagulants.

The other therapeutic agent may be a coagulant. This may be used especially when the compound of the invention has an anticoagulant activity.

The other therapeutic agent may be a natural or synthetic vitamin K (e.g. vitamin $K_3$ or, more particularly, vitamin $K_1$, $K_2$, $K_4$ or $K_5$). The invention also relates to a combination of a compound of formula I with a coagulant, such as vitamin K (e.g. vitamin $K_3$ or, more particularly, vitamin $K_1$, $K_2$, $K_4$ or $K_5$). There is also provided by the present invention a process of preparing a combination treatment for osteoporosis and/or osteopenia, wherein the compound of formula I is combined with a coagulant such as vitamin K (e.g. vitamin $K_3$ or, more particularly, vitamin $K_1$, $K_2$, $K_4$ or $K_5$), and optionally a pharmaceutical excipient, carrier or diluent.

In another aspect the other therapeutic agent may be vitamin D, in one aspect as either vitamin D3 or vitamin D2 forms.

In another aspect the other therapeutic agent may be vitamin B1, or B2, or B6 or other trace vitamins or vitamin-like compounds such as folic acid or pantothenic acid.

In another aspect the other therapeutic agent may be vitamin C or vitamin A.

In another aspect the other therapeutic agent may be a mineral, such as calcium and magnesium (e.g. magnesium).

In another aspect the other therapeutic agent may be a, bisphosphonate drug, teriparatide, strontium ranelate or oestrogen replacement therapy (i.e. osestrogen).

The invention also relates to the compound of formula I, or combination of the compound of formula I and a coagulant (e.g. vitamin $K_1$, $K_2$, $K_4$ or $K_5$), in a combination with one or more compounds selected from the list consisting of: calcium, magnesium, a bisphosphonate drug, teriparatide, strontium ranelate or oestrogen replacement therapy, or, more particularly, vitamin D, vitamins B1, B2, B6 or other vitamin-like compounds, such as, but not limited to, pantothenic acid or folic acid or combinations of the above.

In a further aspect, the compound of the invention is used with vitamin K (e.g. vitamin $K_1$, $K_2$, $K_4$ or $K_5$) and one or more other vitamins or vitamin like compounds, such as vitamin B1, or B2, or B6 or other trace vitamins or vitamin like compounds such as folic acid or pantothenic acid.

The compounds may be used together as a combined preparation for simultaneous, separate or sequential use in therapy for osteoporosis and/or osteopenia. For example, the compound of formula (I) may be delivered orally and a coagulant may be delivered intravenously.

In one aspect the invention relates to a method of preparing a combined medicine, the method comprising combining a coagulant, for example vitamin K, with the compound of formula (I).

In accordance with the invention, compounds of formula (I) may be administered alone (i.e. as a monotherapy, such as a monotherapy for the prevention or treatment of osteoporosis and/or osteopenia). In alternative embodiments of the invention, however, compounds of formula (I) may be administered in combination with another therapeutic agent.

Thus further aspects of the invention relate to a combination product comprising:
(A) a compound of formula (I), as hereinbefore defined, and
(B) another therapeutic agent (e.g. vitamin C, vitamin A or, more particularly, calcium, magnesium, a bisphosphonate drug, teriparatide, strontium ranelate, oestrogen replacement therapy, a coagulant (such as vitamin $K_1$, $K_2$, $K_4$ or $K_5$), vitamin D (such as vitamin D3 or vitamin D2), vitamin B1, or B2, or B6 or other trace vitamins or vitamin-like compounds such as folic acid or pantothenic acid), wherein each of components (A) and (B) is formulated in admixture with a pharmaceutically-acceptable adjuvant, diluent or carrier.

When used herein, the term "another therapeutic agent" includes references to one or more (e.g. one, two or three) therapeutic agents (e.g. one or two therapeutic agents) selected from a mineral, a bisphosphonate drug, teriparatide, strontium ranelate, oestrogen replacement therapy or, more particularly, a coagulant or a vitamin.

Particular other therapeutic agents that may be mentioned include, for example, calcium, magnesium, a bisphosphonate drug, teriparatide, strontium ranelate, oestrogen replacement therapy or, more particularly, the coagulant, vitamin K (such as vitamin $K_1$, $K_2$, $K_4$ or $K_5$), and vitamins such as vitamin C, vitamin A or, more particularly, vitamin D (such as vitamin D3 or vitamin D2), vitamin B1, or B2, or B6 or other trace vitamins or vitamin-like compounds such as folic acid or pantothenic acid.

Thus further aspects of the invention relate to a combination product comprising:
(I) a compound of formula (I), as hereinbefore defined, and
(II) a coagulant (e.g. vitamin $K_1$, $K_2$, $K_4$ or $K_5$),
(III) one or more (e.g. three, two or, more particularly, one) agents selected from vitamin C, vitamin A or, more particularly, calcium, magnesium, a bisphosphonate drug, teriparatide, strontium ranelate, oestrogen, vitamin D (such as vitamin D3 or vitamin D2), vitamin B1, or B2, or B6 or other trace vitamins or vitamin-like compounds such as folic acid or pantothenic acid,
wherein each of components (I), (II) and (III) is formulated in admixture with a pharmaceutically-acceptable adjuvant, diluent or carrier.

A particular combination product that may be mentioned herein comprises:
(AA) a compound of formula (I), as hereinbefore defined,
(BB) vitamin K (e.g. vitamin $K_1$, $K_2$, $K_4$ or $K_5$),
(CC) calcium, and
(DD) vitamin D,
wherein each of components (AA), (BB), (CC) and (DD) is formulated in admixture with a pharmaceutically-acceptable adjuvant, diluent or carrier.

When used herein, the term "administered sequentially, simultaneously or concomitantly" includes references to:
administration of separate pharmaceutical formulations (one containing the compound of formula I and one or more others containing the one or more other therapeutic agents); and
administration of a single pharmaceutical formulation containing the compound of formula I and the other therapeutic agent(s).

The combination product described above provides for the administration of component (A) in conjunction with component (B), and may thus be presented either as separate formulations, wherein at least one of those formulations comprises component (A) and at least one comprises component (B), or may be presented (i.e. formulated) as a combined preparation (i.e. presented as a single formulation including component (A) and component (B)). Combination products containing more than two components (e.g. ones containing components (I), (II) and (III) or (AA), (BB), (CC) and (DD)) as described above may be presented by analogy.

Thus, there is further provided:
(I) a pharmaceutical formulation including a compound of formula I, as hereinbefore defined and another therapeutic agent, in admixture with a pharmaceutically-acceptable adjuvant, diluent or carrier (which formulation is hereinafter referred to as a "combined preparation"); and
(II) a kit of parts comprising components:
  (i) a pharmaceutical formulation including a compound of formula I, as hereinbefore defined, in admixture with a pharmaceutically-acceptable adjuvant, diluent or carrier; and
  (ii) a pharmaceutical formulation including another therapeutic agent, in admixture with a pharmaceutically-acceptable adjuvant, diluent or carrier,
    which components (i) and (ii) are each provided in a form that is suitable for administration in conjunction with the other.

Component (i) of the kit of parts is thus component (A) in admixture with a pharmaceutically-acceptable adjuvant, diluent or carrier. Similarly, component (ii) is component (B) in admixture with a pharmaceutically-acceptable adjuvant, diluent or carrier. Reference to other combinations can be made by analogy (e.g. three or four component combinations).

In one aspect the invention relates to a method of preparing a combined medicine, the method comprising combining a coagulant, for example vitamin K (vitamin $K_1$, $K_2$, $K_4$ or $K_5$), with the compound of formula (I).

Optionally the combined medicine may then be combined with any pharmaceutically acceptable excipient, diluent or carrier to form a pharmaceutical composition.

Optionally the combined medicine or pharmaceutical composition may be formulated into a tablet for oral delivery.

The invention also relates to use of a combination as disclosed above in medicine, specifically in the treatment of osteoporosis, and use of the combination in the preparation of a medicament for the treatment of osteoporosis and/or osteopenia.

In another aspect of the present invention there is provided a method for the treatment or prevention of osteoporosis and/or osteopenia, which comprises administering to a patient in need of treatment a therapeutically effective amount of a compounds or combinations of the invention.

The magnitude of prophylactic or therapeutic dose of a compound of formula (I) will, of course, vary with the nature and the severity of the condition to be treated and with the particular compound of formula I and its route of administration. It will also vary according to a variety of factors including the age, weight, general health, sex, diet, time of administration, rate of excretion, drug combination and response of the individual patient. In general, the daily dose is from about 0.001 mg to about 1000 mg (e.g. 0.001 mg to about 100 mg) per kg body weight of a mammal, preferably 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for the oral administration of humans may contain from 0.05 mg to 5 g of active agent compounded with an appropriate and convenient amount of carrier material which may vary from about 5 to about 99.95 percent of the total composition. Dosage unit forms will generally contain between from about 0.1 mg to about 0.4 g of an active ingredient, typically 0.5 mg, 1 mg, 2 mg, 5 mg, 10 mg, 25 mg, 50 mg, 100 mg, 200 mg, or 400 mg. In any event, the medical practitioner, or other skilled person, will be able to determine routinely the actual dosage, which will be most suitable for an individual patient.

The amount of active ingredient that may be combined with the carrier materials to produce a single dosage form will vary depending upon the host treated and the particular mode of administration. For example, a formulation intended for the oral administration of humans may contain from 0.05 mg to 5 g of active agent compounded with an appropriate and convenient amount of carrier material which may vary from about 5 to about 99.95 percent of the total composition. Dosage unit forms will generally contain between from about 0.1 mg to about 0.4 g of an active ingredient, typically 0.5 mg, 1 mg, 2 mg, 5 mg, 10 mg, 25 mg, 50 mg, 100 mg, 200 mg, or 400 mg.

Preferred doses are of compound of formula (I) are a dose of greater than 40 mg daily, more preferably at least 45 mg daily.

The total daily dose may be delivered in one or more separate doses over the course of the day, alone or in combination with other therapies.

Compounds of formula (I) may be administered by any suitable means, for example orally, by inhalation spray, topically, parenterally or rectally in dosage unit formulations containing conventional non-toxic pharmaceutically acceptable carriers, adjuvants and vehicles. The term "parenteral" as used herein includes subcutaneous injections, intravenous, intramuscular, intrasternal injection or infusion techniques.

The pharmaceutical compositions containing the active ingredient may be in a form suitable for oral use, for example, as tablets, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc.

The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for controlled release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

For example, a solid oral composition such as a tablet or capsule may contain from 1 to 99% (w/w) active ingredient; from 0 to 99% (w/w) diluent or filler; from 0 to 20% (w/w) of a disintegrant; from 0 to 5% (w/w) of a lubricant; from 0 to 5% (w/w) of a flow aid; from 0 to 50% (w/w) of a granulating agent or binder; from 0 to 5% (w/w) of an antioxidant; and from 0 to 5% (w/w) of a pigment. A controlled release tablet may in addition contain from 0 to 90% (w/w) of a release-controlling polymer.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin. The aqueous suspensions may also contain one or more preservatives, one or more colouring agents, one or more flavouring agents, and one or more sweetening agents.

A parenteral formulation (such as a solution or suspension for injection or a solution for infusion) may contain from 1 to 50% (w/w) active ingredient; and from 50% (w/w) to 99% (w/w) of a liquid or semisolid carrier or vehicle (e.g. a solvent such as water); and 0-20% (w/w) of one or more other excipients such as buffering agents, antioxidants, suspension stabilisers, tonicity adjusting agents and preservatives.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents and flavouring agents may be added to provide a palatable oral preparation. These compositions may be preserved by the addition of an anti-oxidant such as ascorbic acid, vitamin E or some such equivalent agent.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a preservative, and flavouring and colouring agents. The pharmaceutical compositions may be in the form of a sterile injectable aqueous or oleagenous suspension. This suspension may be formulated according to the known art using suitable dispersing or wetting agents and suspending agents. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringers solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Compounds of formula (I) may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing the compound of formula (I) are employed. (For purposes of this application, topical application shall include mouth washes and gargles.) Topical formulations may generally be comprised of a pharmaceutical carrier, cosolvent, emulsifier, penetration enhancer, preservative system, and emollient.

LIST OF FIGURES

The invention will now be described, by way of example only, with reference to the accompanying figures, in which:

FIG. 17 shows NaQuinate does not alter normal bone trabecular number

FIG. 18 shows NaQuinate inhibits bone loss in neurectomized limbs

FIG. 19 shows NaQuinate does not alter normal bone volume

FIG. 20 shows NaQuinate inhibits bone loss in neurectomized limbs

A compound according to the present invention may be synthesised by any suitable method. A suitable method is disclosed below with reference to Ruttimann et al "Chimica" (1986) 40 (9) 290-306, and Gerorkzan et al "Chem. Hetrocyclic Compd" (Engl. Trans.) (1989) 2, 269 and FIGS. 8 and 9. In addition, compounds of the invention may be made by analogy to the methods disclosed in GB 2,314,773 and incorporated herein by reference. As will be appreciated, the compounds of the current invention may be prepared by analogy to the methods disclosed in the above-mentioned references or may be bought commercially (where indicated).

Figure 8:
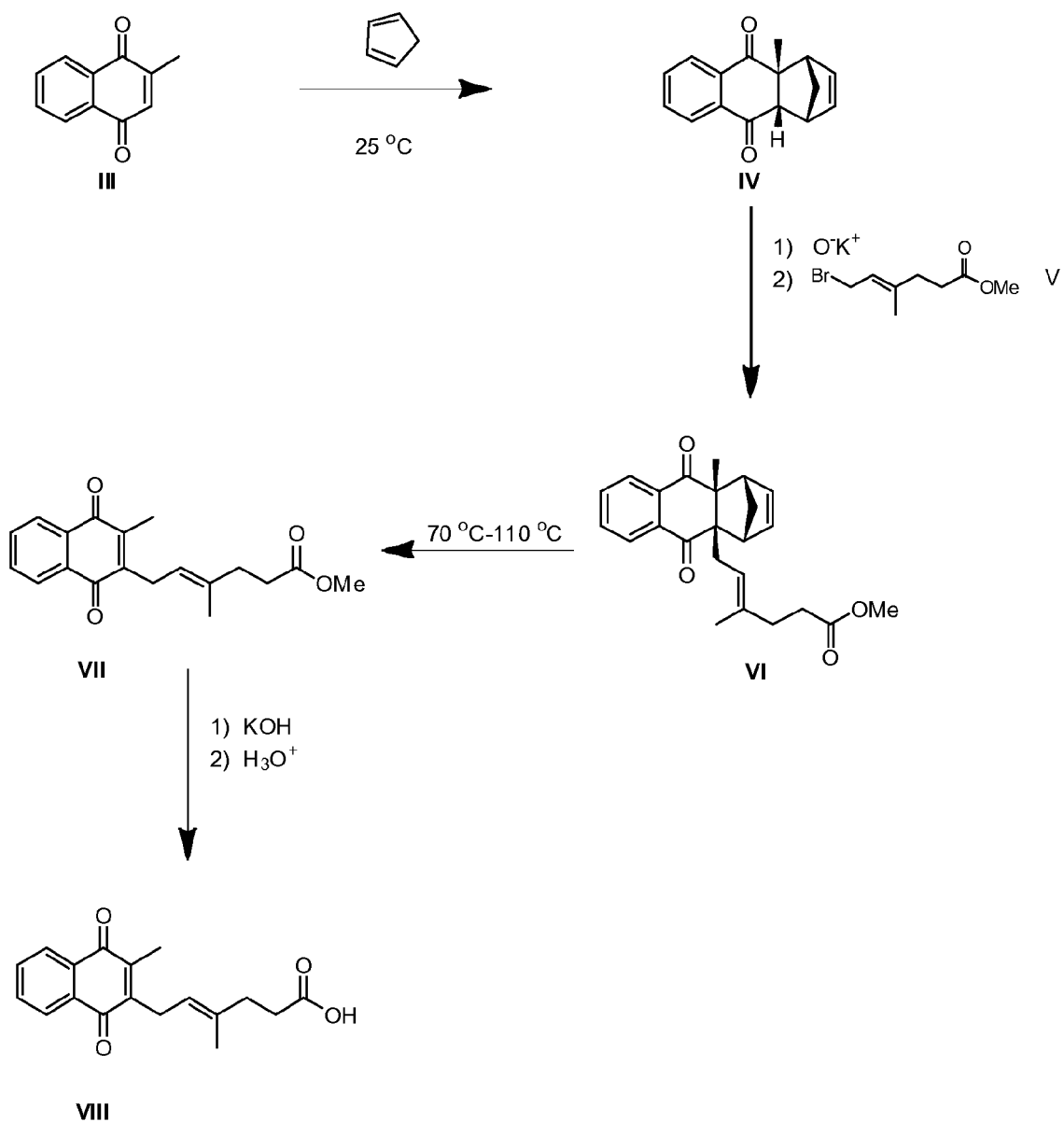
FIG. 8 is an example of a synthetic pathway for a compound of Formula VIII (also called NaQuinate herein)

As shown in FIG. 8 herein, the starting material menadione (Aldrich Chemical Company, Ill) was employed and reacted with cyclopentadiene at 25° C. to generate the fused derivative thereof (IV). Treatment with base, O⁻K⁺ (e.g. potassium tert-butoxide) and subsequent treatment with methyl 4-methyl-6-bromo-hex-4-eneoate (V), introduced the 3-substituent (VI). The intermediate was further reacted by application of heat in the range of 70° C. to 110° C. causing the elimination of cyclopentadiene with the resultant isolation of the product methyl ester NaQuinate (VII). The characterisation of this compound is given by Ruttimann et al as hereinbefore referred, which is incorporated herein by reference.

The compound VII is converted to the corresponding carboxylic acid by means of base hydrolysis, for example using KOH, and subsequent acid treatment for example using $H_3O^+$ (e.g. aqueous hydrochloric acid), or equivalent, in known manner, thereby generating NaQuinate (VIII). The characterisation of this compound is given by Ruttimann et al as hereinbefore referred.

Figure 9A:
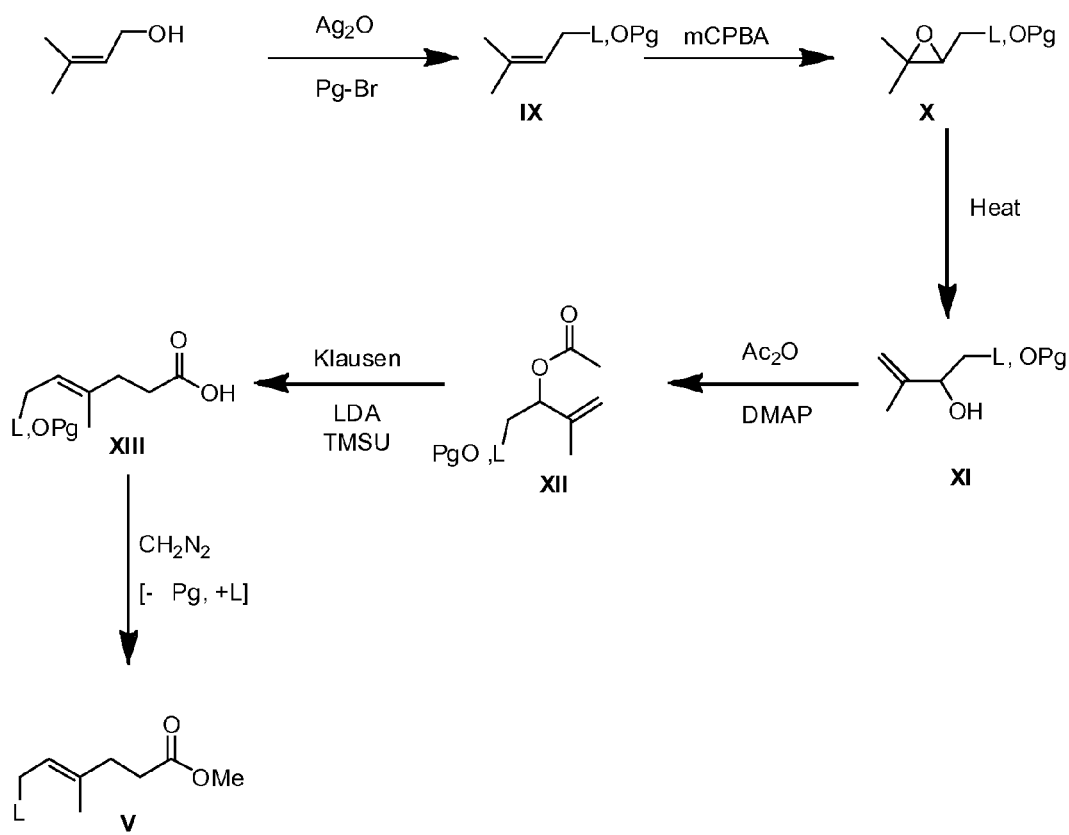
FIG. 9 is an example of a synthetic pathway for a compound V used in the pathway shown in FIG. 8.

The preparation of intermediate (V) used above is carried out as shown in FIG. 9A. Prenyl bromide (Aldrich Chemical Company) (IX wherein L=Br) was converted to the epoxide using mCPBA, which was subsequently heated to derive the intermediate (X) wherein L=Br. Treatment with Ac₂O-DMAP generated the ester (XII) wherein L=Br, which was then subject to Claisen (e.g. Ireland-Claisen) rearrangement using standard reagents such as LDA and TMSCI (referred to in FIG. 2A as TMSU). The rearranged product thereof (XIII) wherein L=Br was converted to the methyl ester (V) by reaction with $CH_2N_2$ for use in the preparation of NaQuinate as hereinbefore defined. The characterisation thereof is provided by Gerorkzan et al as hereinbefore referred, which disclosure is incorporated herein by reference.

Figure 9B:
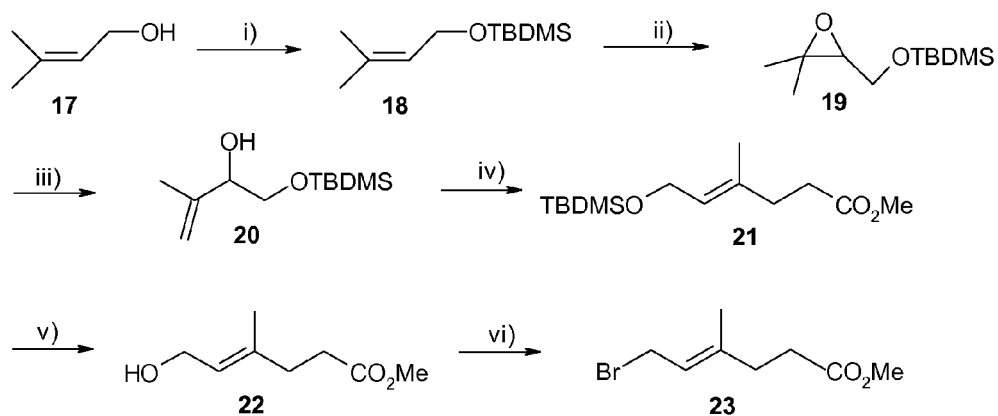
Figure 10:
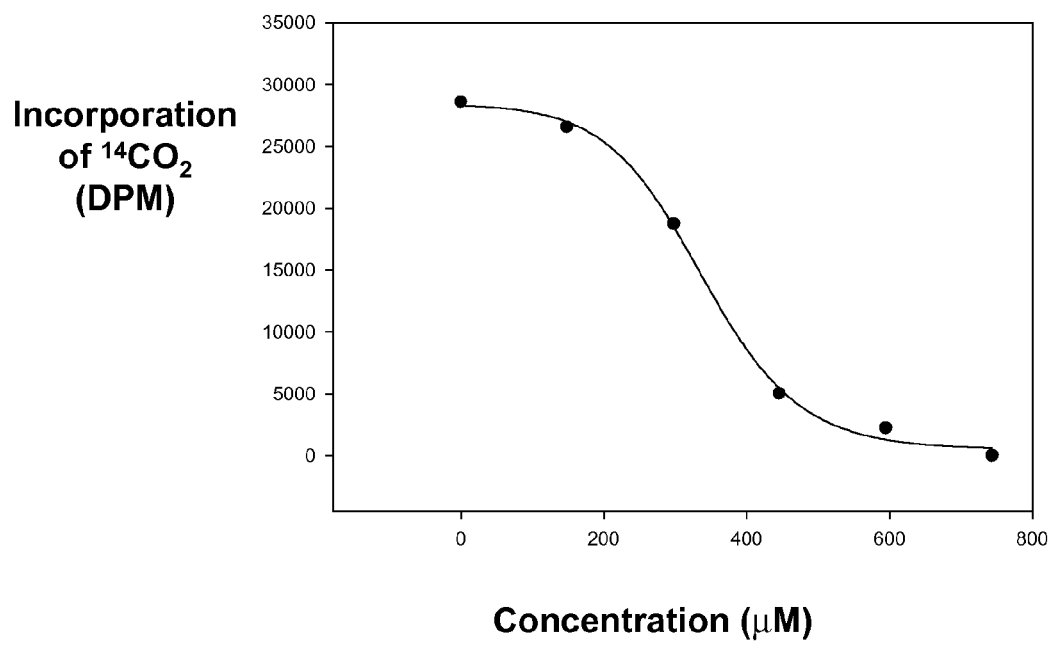
FIG. 10 shows the Inhibition of γ-carboxylase by KCAT-5C(XIV) in the presence of 220 µM vitamin $K_1$ hydroquinone (n=1)
Figure 11:
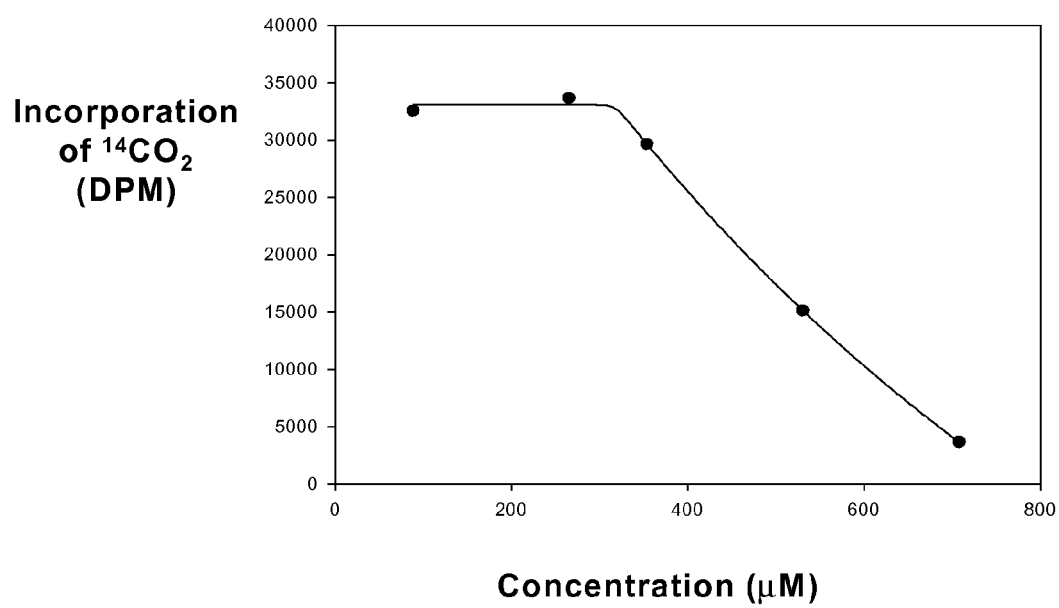
FIG. 11 shows the inhibition of γ-carboxylase by KCAT-5C-Me (XIX) in the presence of 220 µM vitamin $K_1$ hydroquinone (n=1)
Figure 12:
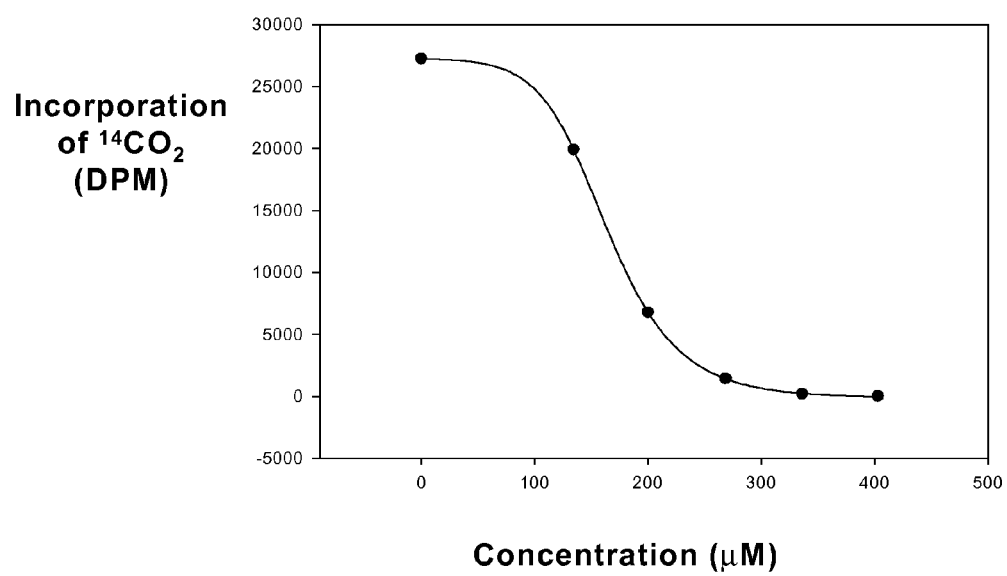
FIG. 12 shows the inhibition of γ-carboxylase by NaQuinate (VIII) in the presence of 220 µM vitamin $K_1$ hydroquinone (n=1)
Figure 13:
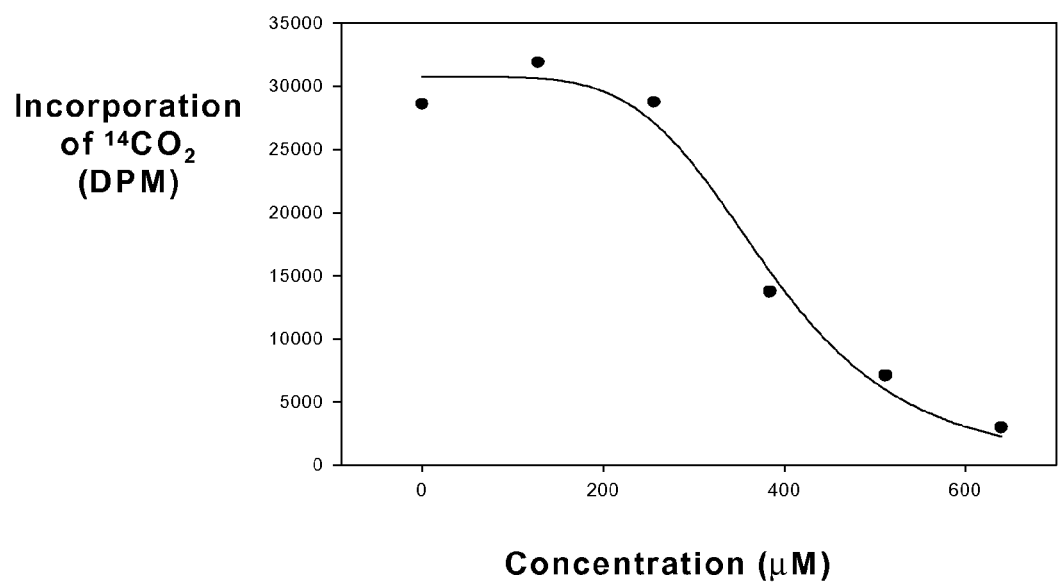
FIG. 13 shows the inhibition of γ-carboxylase by NaQuinate-Me (VII) in the presence of 220 µM vitamin $K_1$ hydroquinone (n=1)
Figure 14:
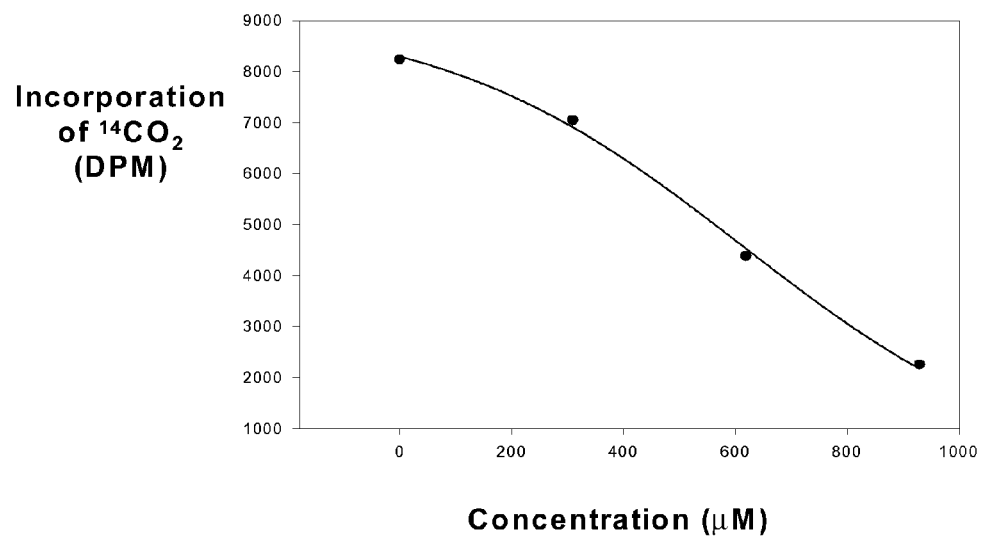
FIG. 14 shows the inhibition of γ-carboxylase by QCAT-Me (XVIII) in the presence of 220 µM vitamin $K_1$ hydroquinone (n=1)
Figure 15:
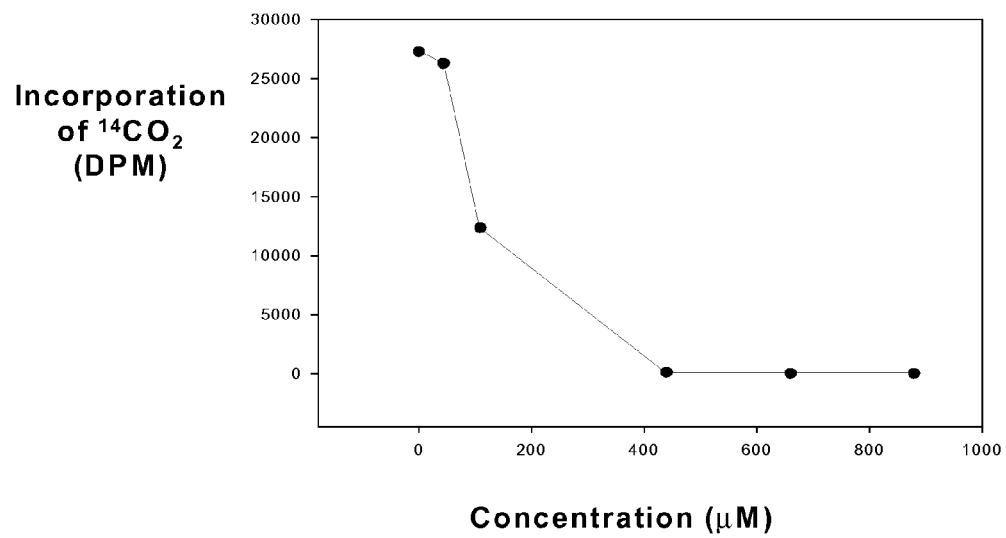
FIG. 15 shows the inhibition of γ-carboxylase by DMK (XVI) in the presence of 220 µM vitamin $K_1$ hydroquinone (n=1)
Figure 16:
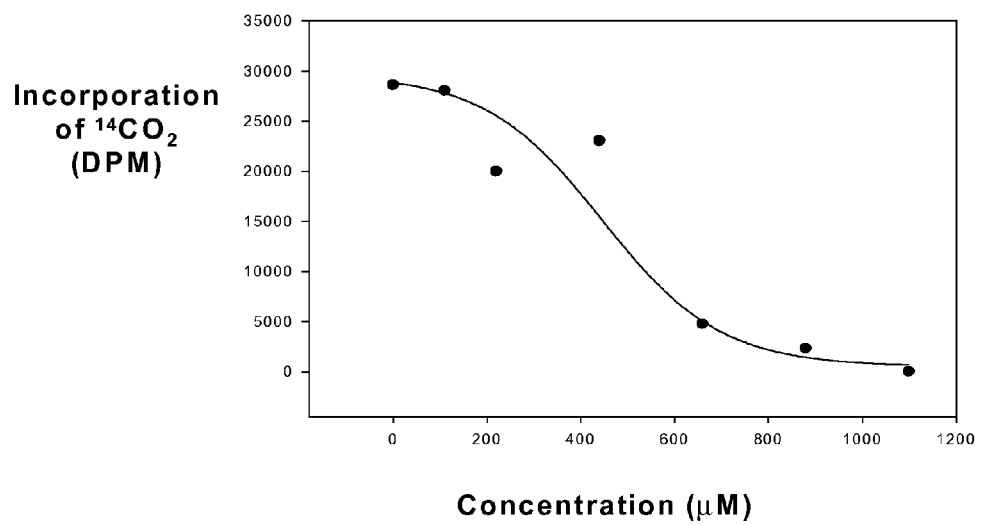
FIG. 16 shows the inhibition of γ-carboxylase by Vitamin $K_3$ in the presence of 220 µM vitamin $K_1$ hydroquinone (n=1)

Alternatively, a more particular preparation of intermediate (V) used above is carried out as shown in FIG. 9B. Prenyl alcohol (17) was protected with tert-butyldimethylsilylchloride (TBDMSCl) to form TBDMS ether 18. Reaction of 18 with meta-chloroperoxybenzoic acid formed epoxide 19, which underwent subsequent rearrangement to form alcohol 20 under high temperature reflux. Reaction of 20 with trimethylorthoacetate in the presence of propionic acid produced ester 21, which was deprotected to provide free alcohol 22 (using tetrabutylammonium fluoride). Subsequent functional group interconversion of 22 to the bromide 23 (also referred to herein as compound (V)) was achieved using carbon tetrabromide and triphenylphosphine.

Equivalent methods may be used to make other compounds within the scope of the present invention.

Determining Biological Activity: The various compounds of formula I can be tested using the following assays to determine their activity in inhibition of bone loss:

1. Use of compounds in the prevention of the release of IL-6, suitably from an osteoblast-like cell line, for example, MG63 as disclosed in the examples herein. In one aspect the compounds of the invention have an $IC_{50}$ of $2-5\times10^{-7}$M or less in such an experiment.

2. Use of compounds in the inhibition of bone loss in oestrogen deficient rodents, as disclosed in the examples herein. In one aspect the compounds of the invention are able to prevent loss of bone density when compared with an oviarectomized control rodent.

The teaching of all references in the present application, including patent applications and granted patents, are herein fully incorporated by reference. Any patent application to which this application claims priority is incorporated by reference herein in its entirety in the manner described herein for publications and references.

For the avoidance of doubt the terms 'comprising', 'comprise' and 'comprises' herein is intended by the inventors to be optionally substitutable with the terms 'consisting of', 'consist of', and 'consists of', respectively, in every instance. The term "about" (or "around") where used in all numerical values allows for a 5% variation, i.e. a value of about 1.25% would mean from between 1.19%-1.31%.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims. All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the measurement, the method being employed to determine the value, or the variation that exists among the study subjects.

The term "or combinations thereof" as used herein refers to all permutations and combinations of the listed items preceding the term.

Elements for use in combination may be combined within the same formulation, for simultaneous delivery, or may be used separately, either delivered concomitantly or sequentially, and refer to combinations herein contemplates all such possibilities.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

Any individual aspect of the invention may be combined with any other aspect, except where apparent from the context.

The invention will be further described by reference to the following, non-limiting, examples:

EXAMPLES

1. There are numerous factors that regulate bone physiology. Targeting the agents that induce bone resorption by recruiting/activating the cells that induce bone loss (the osteoclasts) has had limited exposure/efficacy. Most current therapies target the osteoclasts once they have been recruited or activated. A family of locally (bone) produced proteins called cytokines can induce a range of stimuli that can affect osteoclast number/activity. One of these cytokines is called interleukin-6 (IL-6). IL-6 is released by many cell types, including the bone forming cells (osteoblasts), following challenge from a range of agonists. These agonists can be physiological $(1,25(OH)_2$ vitamin D3, interleukin-1β) or pathophysiological (interleukin-1β; bacterial endotoxin).

Figure 1:
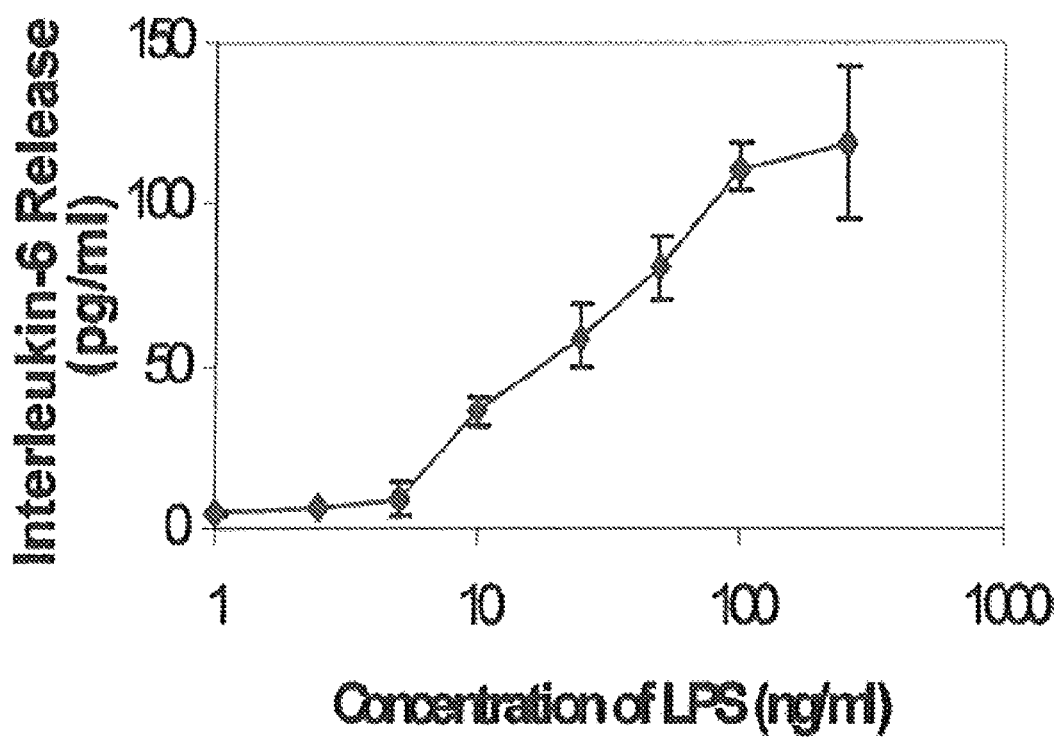
FIG. 1 is a graph showing concentration-dependent release of interleukin-6 from cultured MG63 osteoblast-like cells by *E. coli* lipopolysaccharide (LPS)
Figure 2:
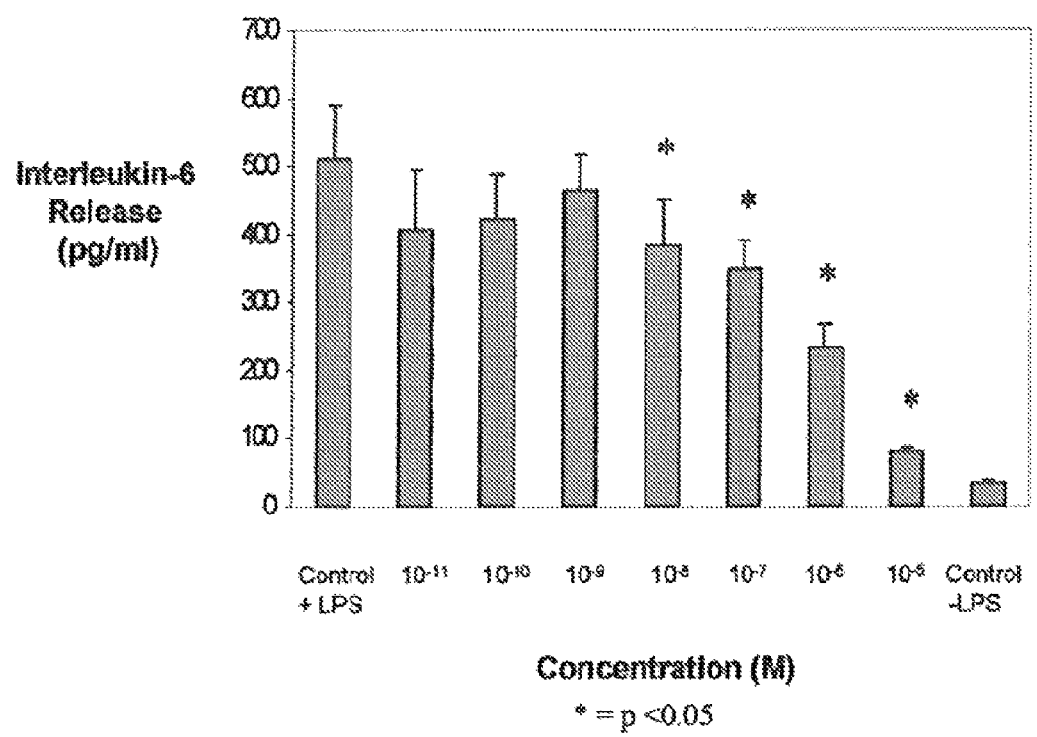
FIG. 2 is a graph of concentration-dependent inhibition of *E. coli* LPS-stimulated (25 ng/ml) interleukin-6 release from MG63 osteoblast-like cells by NaQuinate.

In vitro studies focussed on an immortalised osteoblast-like cell line called MG63 that was derived from a human osteosarcoma (bone cancer). These cells were cultured and screened for their ability to synthesize and release a range of cytokines including IL-6. Due to the well described activities of IL-6 induced bone loss this cytokine was focussed upon (see Manolagas S. C., Ann N Y Acad. Sci. 1998 May 1; 840:194-204). The release of IL-6 by cultured MG63 cells under the influence of the agonists described above was considered. Although all three agonists cause IL-6 release from cultured MG63 cells in a concentration-dependent manner, for ease of manipulation of experimental conditions and management of costs, bacterial lipopolysaccharide (LPS; E. coli) was the agonist that was used. As is shown in FIG. 1, IL-6 is released from cultured MG63 cells in a concentration dependent manner by LPS. These data were used to define the conditions for further studies; specifically, the concentration of bacterial lipopolysaccharide that induced a 50% of maximal IL-6 response from MG63, which was used as the challenge conditions for studies with the compound of the present invention. As can be seen in FIG. 2 one compound of the present invention (4E)-6-(1,4-dihydro-2-methyl-1,4-dioxonaphthalen-3-yl)-4-methylhex-4-enoic acid (VIII) (also called NaQuinate herein in this example) inhibits stimulated IL-6 release from cultured MG63 cells in a concentration-dependent manner with an $IC_{50}$ of $2-5\times10^{-7}$M. IL-6 can be measured by commercial immunoassays, for example, the QuantiGlo IL-6 Immunoassay from R&D systems.

Figure 3:
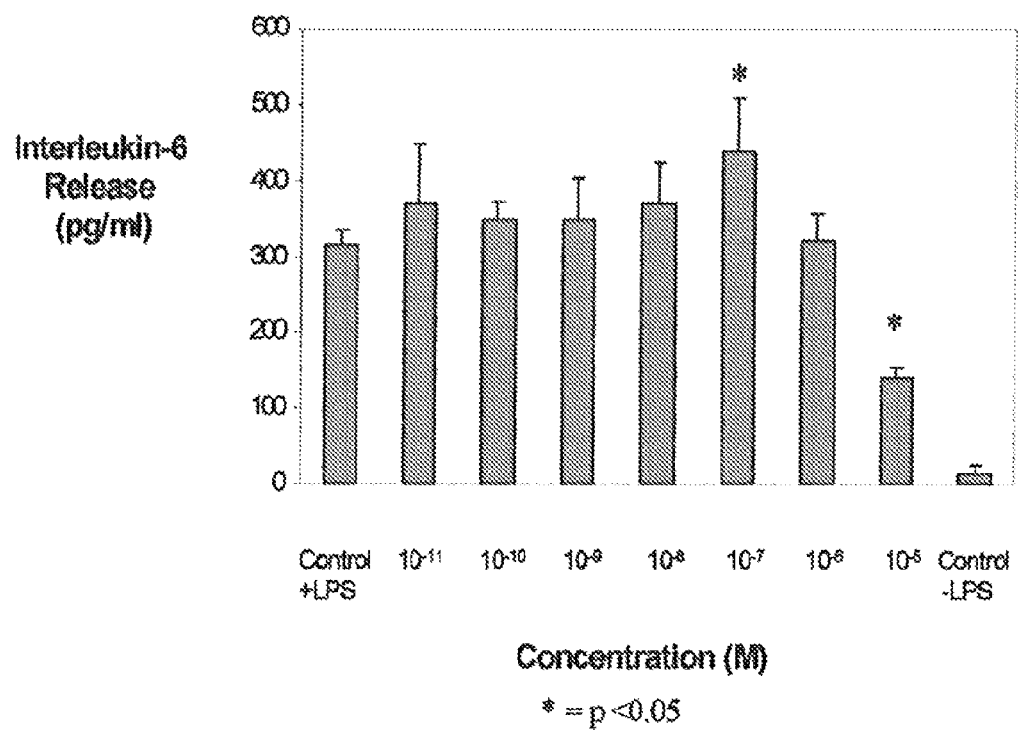
FIG. 3 shows a graph of concentration-dependent inhibition of *E. coli* LPS-stimulated (25 ng/ml) interleukin-6 release from MG63 osteoblast-like cells by compound XIV of the present invention which is only active inhibiting Interleukin-6 from cultured MG63 osteoblast-like cells at very high concentrations ($10^{-5}$ M)
Figure 4:
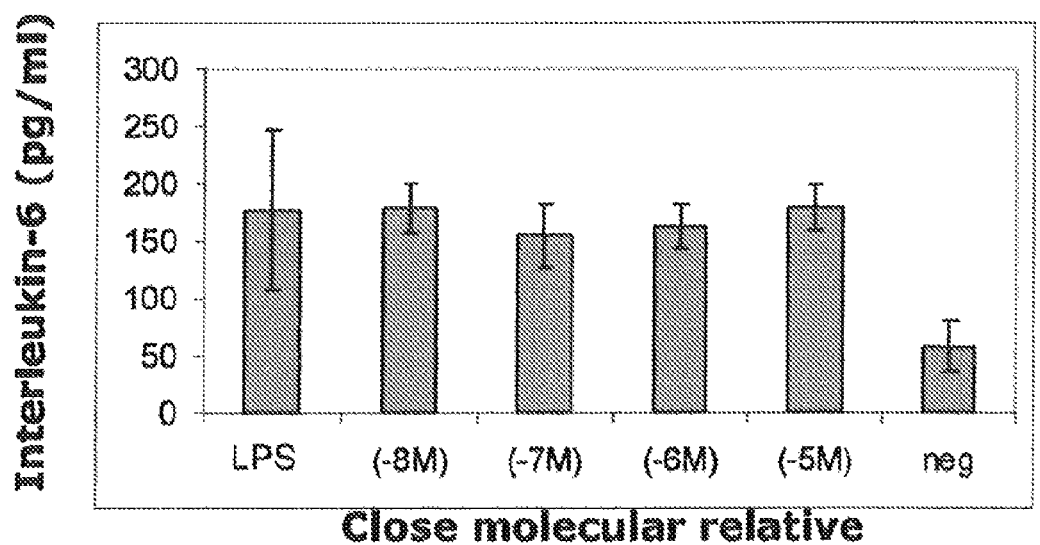
FIG. 4 shows a graph of concentration-dependent inhibition of *E. coli* LPS-stimulated (25 ng/ml) interleukin-6 release from MG63 osteoblast-like cells by compound XV, which can be seen is completely inactive in inhibiting Interleukin-6 from cultured MG63 osteoblast osteoblast-like cells.

The equivalent activity of two different NaQuinate-like molecules, namely (2E)-4-(1,4-dihydro-2-methyl-1,4-dioxonaphthalen-3-yl)-2-methylbut-2-enoic acid (XIV), and and 8-(1,4-dihydro-2-methyl-1,4-dioxonaphthalen-3-yl) octanoic acid (XV), are shown in FIGS. 3 and 4 respectively.

Figure 5:
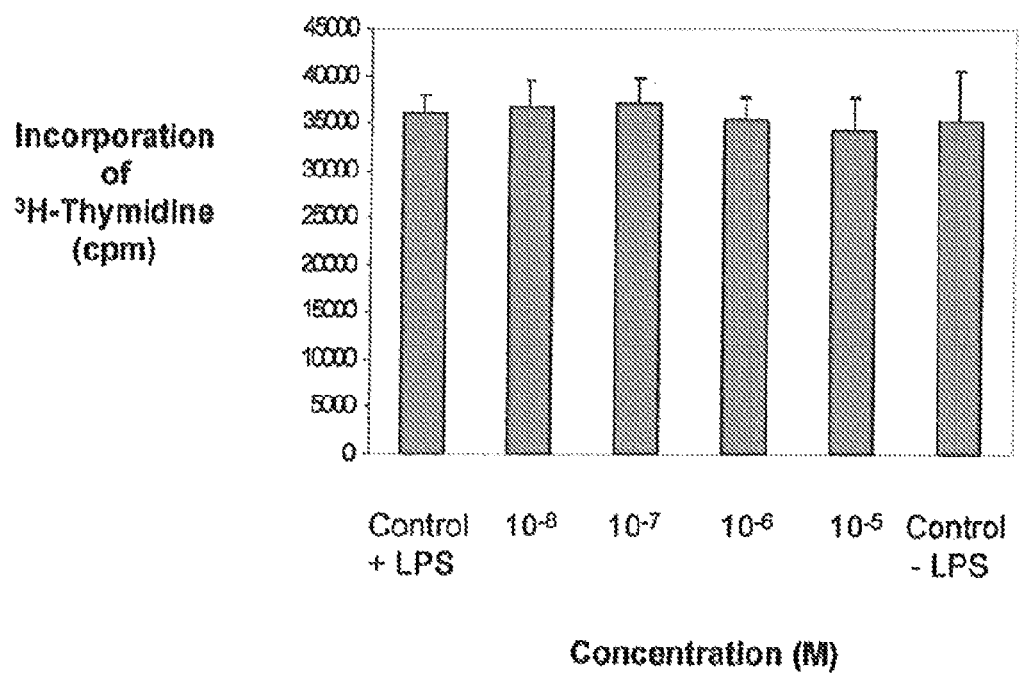
FIG. 5 shows the effect of the compound of the present invention on the viability of the cultured osteoblast-like MG63 cells by measuring the uptake of $^3$H labelled Thymine in the formation of DNA.

The inhibition of IL-6 release is not due to MG63 osteoblast-like cells being killed by NaQuinate as they continue normal DNA synthesis under all concentrations tested (up to $10^{-5}$M), which is considerably outside any therapeutic range. FIG. 5 shows an equivalent incorporation of $^3$H-Thymine between control samples ("control+LPS" and "Control−LPS") of osteoblast-like MG63 cells and those subjected to concentrations of NaQuinate between $10^{-8}$M and $10^{-5}$M. This lack of cell toxicity has also been demonstrated in cultured cell lines derived from skin and liver.

Example 2

The most widely accepted animal model of osteoporosis is the oestrogen deficient rodent, with this model the effect of the present invention has been tested in vivo. All procedures were done under Home Office licence and full local ethical requirements. C57Black mice were randomly assigned to receive total bi-lateral oviarectomy or sham operation. The oviarectomized animals were randomly assigned for treatment or to an untreated control group. At operation eight animals were in each group.

The mice were housed under standard animal house conditions with 12 hour light dark cycles in temperature and humidity controlled conditions for 5 weeks. The Sham and control oviarectomized mice received 10% ethanol in saline vehicle injections intraperitoneally once per day. The NaQuinate treated mice received a single injection (15 μg/mouse/day) administered in 10% ethanol in saline injections intraperitoneally. All mice received the same volume of test sample and this complied with Home Office regulations.

Figure 6A:
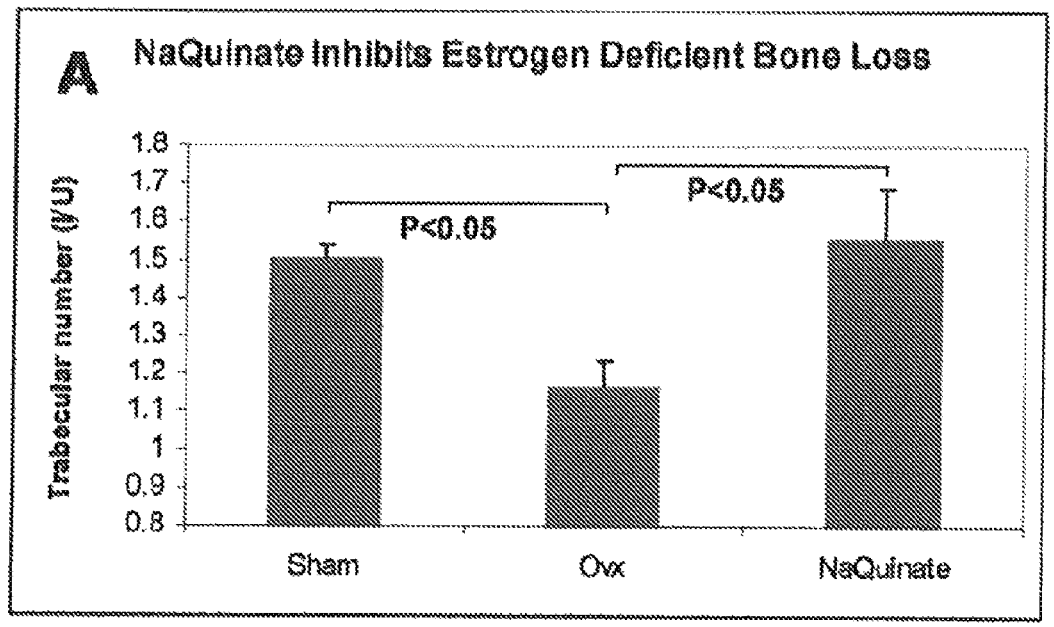
FIG. 6A shows quantified µCT data from the trabecular compartment of mice tibiae (in the form of trabecular number) in Sham operated mice (ie those after a sham operation), Oviarectomized (OVx) mice and OVx animals treated with 15 µg/mouse/day of the compound of the present invention.
Figure 6B:
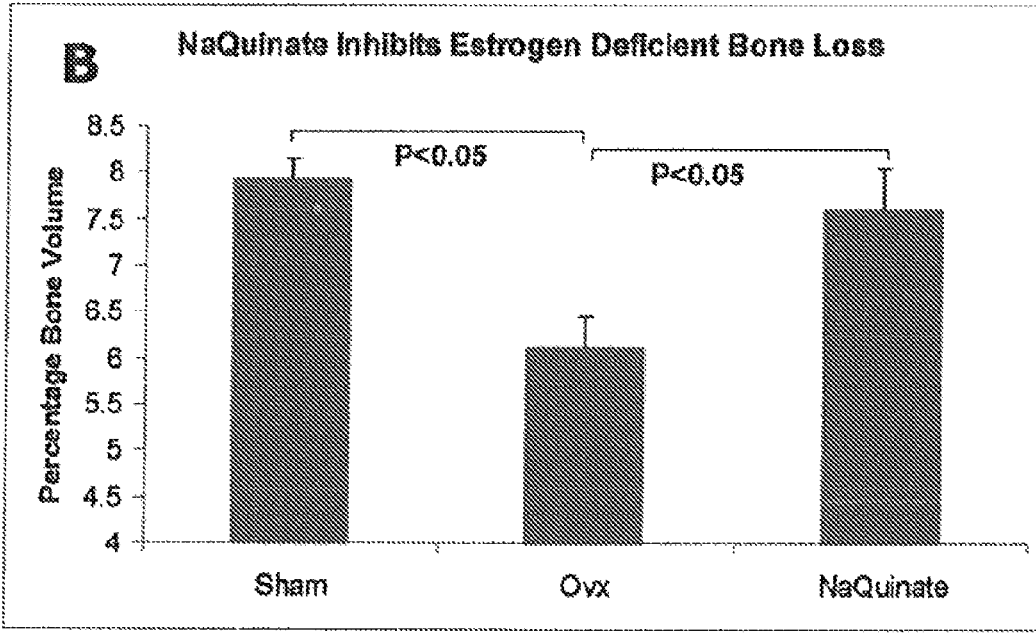
FIG. 6B shows quantified µCT data from the trabecular compartment of mice tibiae (in the form of percentage bone volume) in Sham operated mice, Oviarectomized (OVx) mice and OVx animals treated with 15 µg/mouse/day of the compound of the present invention.
Figure 7A:
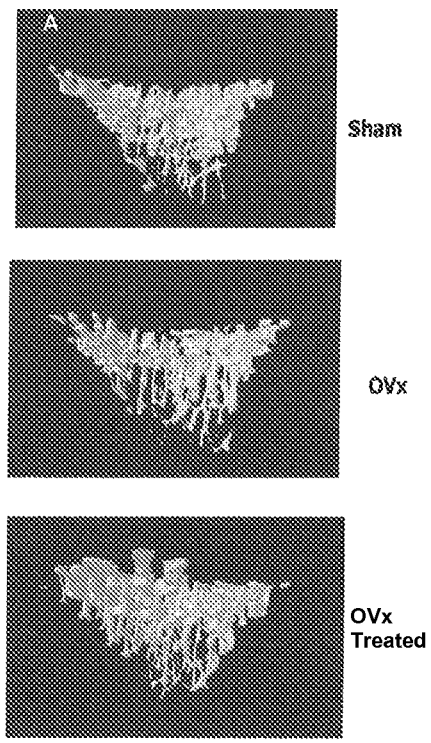
FIG. 7A shows anterior-posterior X-ray µCT image of trabecular compartment of sham mice, OVx mice and OVx mice treated with NaQuinate following Oviarectomy.
Figure 7B:
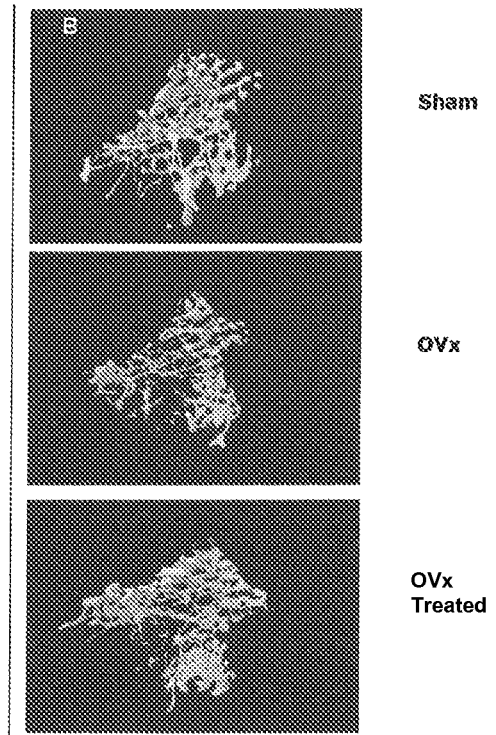
FIG. 7B are Coronal ankle to knee X-ray µCT image of trabecular compartment of sham mice, OVx mice and OVx mice treated with NaQuinate following Oviarectomy.

After 5 weeks treatment the animals were sacrificed by a Schedule 1 method and the tibiae removed for X-ray micro-Computer Tomography (μCT) imaging analyses. As can be seen using trabecular number (in FIG. 6A) and percentage bone content in the trabecular compartment (in FIG. 6B) the administered dose of NaQuinate completely attenuated the bone loss induced by oviarectomy that was seen in the control oviarectomized animals. These observations are presented in FIGS. 7A and B as μCT images. FIG. 7A shows the anterior-posterior view of the tibial trabecular compartment, FIG. 7B shows a coronal view from ankle to knee.

Example 3

NaQuinate Inhibits the Vitamin K-Dependent Enzyme Gamma-Carboxylation Reaction

The activity of NaQuinate and related compounds was examined in the vitamin K cycle.

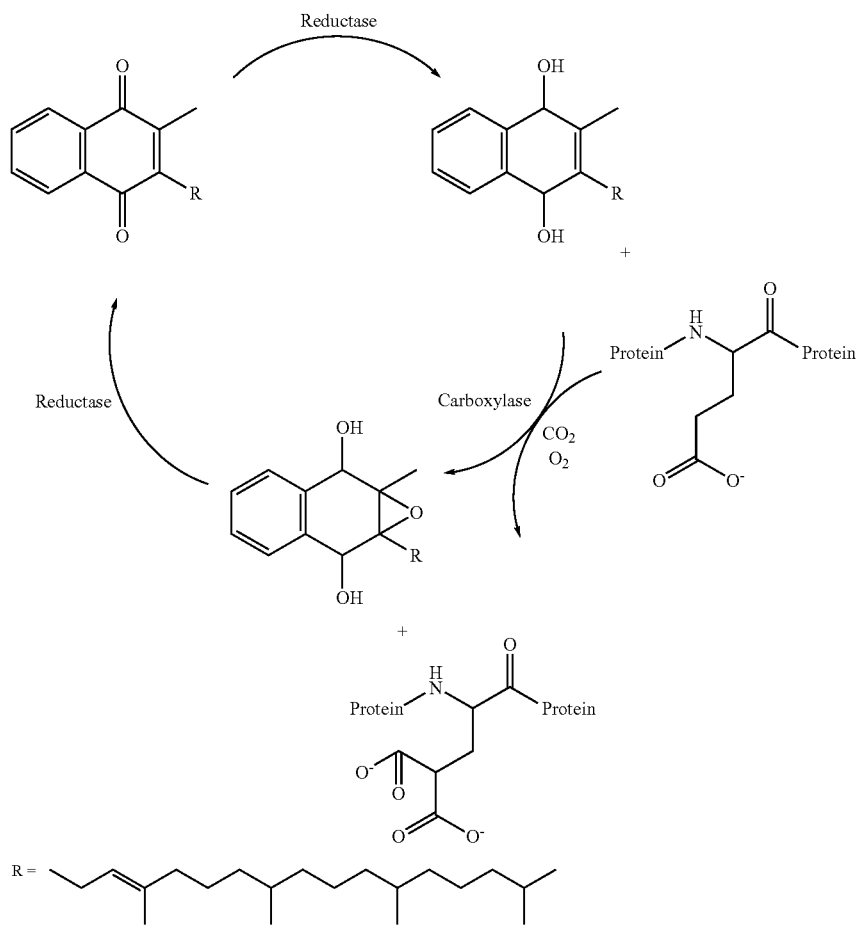

The Vitamin K cycle for Vitamin $K_1$

Carboxylase Assay

The method of Houben et al (Houben, R. J. et al (1997). "Assay of Vitamin K-Dependent Carboxylase Activity in Hepatic and Extrahepatic Tissues." *Methods in Enzymology* 282: 358-368) was used. All the experimental tubes were prepared by the addition of 25 µl of bovine microsome preparation, 5 µl of 10% 3-[(3-cholamidopropyl)dimethylammonio]-2-hydroxy-1-propanesulphonic acid (CHAPS), 25 µl of saturated ammonium sulphate solution and 5 µl of 0.1M dithiothreitol (DTT) (Sigma), 25 µl of saturated ammonium sulphate (Sigma) solution and 5 µl of 500 µM decarboxylated osteocalcin (d-Oc). As the compounds were dissolved in 10 µl of Dimethyl sulphoxide (DMSO), 10 µl of DMSO was added to the positive and negative control tubes. Buffer D (500 mM NaCl and 25 mM Tris-HCl (pH 7.5)) was added to each tube to give a uniform volume of reaction mixture (125 µl). The compounds (KCAT-5C(XIV), KCAT-5C-MeXIX, NaQuinate (VIII), NaQuinate-Me (VII), QCAT-Me (XVIII), DMK (XVI) and vitamin K3 (III)) or vitamin K1 (at a concentration of 889 µM) (Konakion®, mixed micelles from Hoffmann-La Roche) were added to the respective tubes apart from the negative control. The reaction was initiated immediately by the addition of 5 µl of $NaH^{14}CO_3$ (New England Nuclear) solution (to give a final radioactivity of 5 µCi per tube) to each tube. The tubes were mixed with a vortex and placed in a water bath (20° C.) for 30 minutes. 100 µl of each mixture was pipetted into a vial containing 800 µl of 5% (w/v) trichloroacetic acid (TCA) in order to precipitate the protein and stop the reaction. Unincorporated $^{14}CO_2$ was removed by boiling for 3 minutes. After cooling, 5 ml of Optifluor was added and the level of $^{14}CO_2$ incorporation was measured on a Wallac 1414 winspectral liquid scintillation counter.

Inhibition of Recombinant Human Gamma-Carboxylase

Preparation of Compounds

The compounds to be tested were reduced to their hydroquinone forms by the addition of 0.2M DTT to a solution of the compounds in DMSO (giving a final v/v ratio of 1:3 DTT:DMSO) and overnight incubation in a water bath (37° C.).

Carboxylase Assay

In this assay a different microsomal preparation was used than the one described above. This microsomal preparation consists of microsomes prepared from *Trichoplusia ni* High Five cells that had had the cDNA for the human γ-carboxylase incorporated into their DNA. These microsomes were taken from stores that had been prepared as described by Houben, R. J., D. Jin, et al. (1999). "Osteocalcin binds tightly to the gamma-glutamylcarboxylase at a site distinct from that of the other known vitamin K-dependent proteins." *Biochem J* 341 (Pt 2): 265-9.

Standard reaction mixtures contained 5 µl of microsomal preparation, 5 µl of 500 µM decarboxylated osteocalcin (d-OC) (except for the negative control tube), 25 µl of saturated ammonium sulphate solution, 5 µl of 5% PC/CHAPS. In addition to this, 1:3 (v/v) DMSO: 0.2M DTT was added to the tubes (to take into account the fact that the compounds were dissolved in 1:3 DMSO: 0.2M DTT) to give a total volume of 40 µl DMSO: 0.2M DTT per tube. A solution of Buffer D was added to give all final tubes a uniform volume of 125 µl. The experiment was initiated by the addition of 10 µl of a 1:1 (v/v) mixture of vitamin K hydroquinone (final concentration of 220 µM) and $NaH^{14}CO_3$ (final radioactivity of 5 µCi) to each tube, followed by a range of concentrations of the compounds.

Results

Activation of Bovine Liver Gamma-Carboxylase

None of the compounds tested increased the incorporation of $^{14}CO_2$ into osteocalcin to a greater extent than the negative control. It can therefore be concluded that none of the compounds had any activity as a cofactor for γ-carboxylase.

Inhibition of Recombinant Human Gamma-Carboxylase

All the compounds tested were found to inhibit the γ-carboxylase enzyme in the presence of reduced vitamin K1. Concentration-response curves are shown below. Results are expressed as incorporation of $^{14}CO_2$ against concentration of the compound under test and are illustrated in FIGS. 11-16.

The results are summarised as follows:

Inhibitory activity of test compounds ranked according to inhibitory activity

| Compound | $IC_{50}$ against 220 µM vitamin K1 (µM) |
| --- | --- |
| DMK (XVI) | 82.5 |
| NaQuinate (VIII) | 152 |
| KCAT-5C (XIV) | 340 |
| NaQuinate-Me (VII) | 358 |
| Vitamin K3 (III) | 460 |
| KCAT-5C-Me (XIX) | 514 |
| QCAT-Me (XVIII) | 534 |

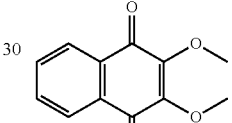

2,3-dimethoxy-1,4-naphthoquinone (DMK, XVI)
Vitamin K3 = menadione (III)

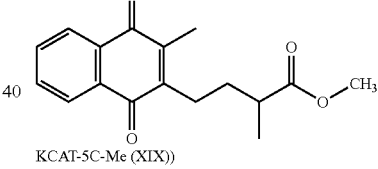

KCAT-5C-Me (XIX))

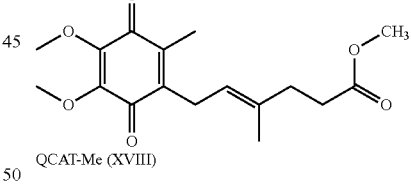

QCAT-Me (XVIII)

The present invention relates to all specific compounds in the examples, for uses as disclosed herein.

Example 4

Disuse Osteopenia/Disuse Osteoporosis

Sciatic Neurectomy

Disuse osteoporosis was induced by right side sciatic neurectomy (SN). Mice were anaesthetized with oxygen and halothane and SN was achieved by resecting a 3-4 mm segment of the sciatic nerve posterior to the hip joint. On the 4th day after surgery mice were treated with either; control or NaQuinate for 5 days/week for 2 weeks. The tibias of both limbs were analysed by micro computerized tomography (µCT). The results of the experiments are shown in FIGS. 17-20.

NaQuinate inhibits bone loss in neurectomized limbs as assessed by % bone volume and trabecular number.

The invention claimed is:
1. A compound of formula (I)

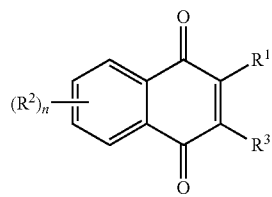

wherein:
R¹ represents hydrogen, halogen, cyano, trifluoromethyl, nitro, —OR$^a$, SR$^a$, SOR$^a$, —SO$_2$R$^a$, —SO$_2$NR$^a$R$^b$, —NR$^a$R$^b$, —NR$^a$COR$^b$, —NR$^a$CO$_2$R$^b$, —COR$^a$, —CO$_2$R$^a$, —CONR$^a$R$^b$, or a hydrocarbon group comprising a straight chain, branched or cyclic group each containing up to 18 carbon atoms, or a heterocyclic group containing up to 18 carbon atoms and at least one heteroatom;
R² represents, independently at each occurrence, hydrogen, halogen, cyano, trifluoromethyl, nitro, —OR$^a$, SR$^a$, SOR$^a$, —SO$_2$R$^a$, —SO$_2$NR$^a$R$^b$, —NR$^a$R$^b$, —NR$^a$COR$^b$, —NR$^a$CO$_2$Rb, —COR$^a$, —CO$_2$R$^a$, —CONR$^a$R$^b$, or a hydrocarbon group comprising a straight chain, branched or cyclic group each containing up to 18 carbon atoms, or a heterocyclic group containing up to 18 carbon atoms and at least one heteroatom;
R³ represents a hydrocarbon group comprising a straight chained, branched or cyclic group each containing up to 18 carbon atoms, and being substituted by at least one moiety including a —CO$_2$R$^a$ substituent;
wherein R$^a$ and R$^b$ independently represent, at each occurrence, hydrogen, or a hydrocarbon group comprising a straight chained, branched or cyclic group each containing up to 18 carbon atoms, or a heterocyclic group containing up to 18 carbon atoms and at least one heteroatom; and
n is 0, 1, 2, 3 or 4;
or a pharmaceutically acceptable solvate salt or prodrug thereof;
for use in the treatment of osteoporosis and/or osteopenia.

2. A method of treating or preventing osteoporosis and/or osteopenia in a patient in need thereof, comprising administering an effective amount of a compound of formula (I) as defined in claim 1, to the patient.

3. A composition comprising a compound of formula (I) as defined in claim 1 and a second therapeutic agent for use in osteoporosis and/or osteopenia.

4. A process of preparing a combination treatment for osteoporosis and/or osteopenia, wherein the compound of formula (I) as defined in claim 1 is combined with a coagulant, and optionally a pharmaceutical excipient, carrier or diluent.

5. The method of claim 2, wherein R¹ represents a hydrocarbon group comprising a straight chain, branched or cyclic group each containing up to 18 carbon atoms.

6. The method of claim 5, wherein R¹ represents methyl.

7. The method of claim 2, wherein n represents 0.

8. The method of claim 2, wherein R³ represents a hydrocarbon group comprising a straight chained or branched hydrocarbon group containing up to 18 carbon atoms substituted by at least one moiety including a —CO$_2$R$^a$ substituent.

9. The method of claim 8, wherein R³ represents $C_{1-9}$ alkyl or $C_{2-9}$ alkenyl, which groups can be straight chained or branched, substituted by at least one moiety including a —CO$_2$R$^a$ substituent.

10. The method of claim 9, wherein R$^a$ of the at least one moiety including a —CO$_2$R$^a$ substituent represents hydrogen or a hydrocarbon group comprising a straight chained or branched hydrocarbon group containing up to 18 carbon atoms.

11. The method of claim 10, wherein R$^a$ of the at least one moiety including a —CO$_2$R$^a$ substituent represents hydrogen or a hydrocarbon group comprising a straight chained or methyl.

12. The method of claim 8, wherein R³ is represented by the following formula (II):

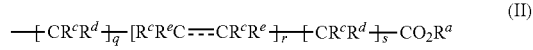

where the unattached bond represents the point of attachment of the structural fragment of formula (II) to the rest of the compound of Formula (I);
R$^a$ is as defined in claim 1;
R$^c$, R$^d$ and R$^e$ are independently selected from hydrogen or $C_{1-6}$ alkyl (which can be straight chained or branched);
q is 1, 2, 3 or 4;
r and s are independently selected from 0, 1, 2, 3 or 4;
===== represents a single or double bond, and when this is a double bond R$^e$ is not present in above formula (II).

13. The method of claim 12, wherein the structural fragment of formula (II) is selected from:

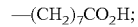

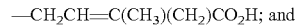

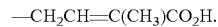

14. The method of claim 2, wherein the compound of formula (I) is
(i) 2,3-dimethoxy-1,4-naphthoquinone (XVI);
(ii) menadione (III);
(iii) KCAT-5C-Me (XIX);
(iv) NaQuinate-Me (VII);
(v) (4E)-6-(1,4-dihydro-2-methyl-1,4-dioxonaphthalen-3-yl)-4-methylhex-4-enoic acid (VIII);
(vi) (2E)-4-(1,4-dihydro-2-methyl-1,4-dioxonaphthalen-3-yl)-2-methylbut-2-enoic acid (XIV); or
(vii) 8-(1,4-dihydro-2-methyl-1,4-dioxonaphthalen-3-yl) octanoic acid (XV).

15. The method of claim 14, wherein the compound of formula (I) is
(a) (4E)-6-(1,4-dihydro-2-methyl-1,4-dioxonaphthalen-3-yl)-4-methylhex-4-enoic acid (VIII);
(b) (2E)-4-(1,4-dihydro-2-methyl-1,4-dioxonaphthalen-3-yl)-2-methylbut-2-enoic acid (XIV); or
(c) 8-(1,4-dihydro-2-methyl-1,4-dioxonaphthalen-3-yl) octanoic acid (XV).

16. The method of claim 15, wherein
the compound of formula (I) is (4E)-6-(1,4-dihydro-2-methyl-1,4-dioxonaphthalen-3-yl)-4-methylhex-4-enoic acid (VIII).

17. The method of claim 2, wherein the osteoporosis is disuse osteoporosis.

18. A method for attenuating bone loss or preventing bone loss in a patient in need thereof comprising administering an effective amount of a compound of formula (I) as defined in claim 1 to the patient.

19. A method of increasing bone density in a patient in need thereof comprising administering an effective amount of a compound of formula (I) as defined in claim 1 to the patient.

20. The method of claim 18, wherein the compound of formula (I) is (4E)-6-(1,4-dihydro-2-methyl-1,4-dioxonaphthalen-3-yl)-4-methylhex-4-enoic acid (VIII).

21. The method of claim 19, wherein the compound of formula (I) is (4E)-6-(1,4-dihydro-2-methyl-1,4-dioxonaphthalen-3-yl)-4-methylhex-4-enoic acid (VIII).

22. The method of claim 2, wherein the compound of formula (I) is not vitamin $K_3$.

23. The method of claim 2, comprising administering a pharmaceutical composition comprising the compound of formula (I) as defined in claim 1 and a pharmaceutically acceptable carrier, diluent or excipient.

24. The method of claim 23, wherein the pharmaceutical composition comprises a coagulant.

25. The method of claim 2, wherein:

$R^1$ or $R^2$ represents hydrogen, halogen, cyano, trifluoromethyl, nitro, —$OR^a$, $SR^a$, $SOR^a$, —$SO_2R^a$, —$SO_2NR^aR^b$, —$NR^aR^b$, —$NR^aCOR^b$, —$NR^aCO^2R^b$, —$COR^a$, —$CO_2R^b$, —$CONR^aR^b$, or a hydrocarbon group comprising a straight chain, branched or cyclic group each containing up to 18 carbon atoms, or a heterocyclic group containing up to 18 carbon atoms and at least one heteroatom;

$R^3$ represents a hydrocarbon group comprising a straight chained, branched or cyclic group each containing up to 18 carbon atoms, and being substituted by at least one moiety including a —$CO_2R^a$ substituent;

wherein $R^a$ and $R^b$ independently represent hydrogen, or a hydrocarbon group comprising a straight chained, branched or cyclic group each containing up to 18 carbon atoms, or a heterocyclic group containing up to 18 carbon atoms and at least one heteroatom;

n is 0, 1, 2, 3 or 4.

26. The method of claim 25, wherein $R^1$ represents an alkyl group including straight chained or branched alkyl groups containing from 1 to 9 carbon atoms.

27. The method of claim 25, wherein n represents 4 and $R^2$, at each occurrence, is hydrogen.

* * * * *